(12) United States Patent
Wilding et al.

(10) Patent No.: US 7,892,819 B2
(45) Date of Patent: *Feb. 22, 2011

(54) MESOSCALE POLYNUCLEOTIDE AMPLIFICATION DEVICES

(75) Inventors: Peter Wilding, Paoli, PA (US); Larry J. Kricka, Berwyn, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 1629 days.

This patent is subject to a terminal disclaimer.

(21) Appl. No.: 10/639,186

(22) Filed: Aug. 11, 2003

(65) Prior Publication Data

US 2011/0020876 A1 Jan. 27, 2011

Related U.S. Application Data

(60) Continuation of application No. 08/745,771, filed on Nov. 8, 1996, now Pat. No. 6,660,517, which is a division of application No. 08/338,728, filed on Nov. 14, 1994, now Pat. No. 5,587,128, which is a continuation-in-part of application No. 08/308,199, filed on Sep. 19, 1994, now Pat. No. 5,498,392, which is a continuation of application No. 07/877,662, filed on May 1, 1992, now abandoned.

(51) Int. Cl.
*C12M 1/34* (2006.01)
*C12M 3/00* (2006.01)
*C12M 1/22* (2006.01)
*B01L 3/00* (2006.01)

(52) U.S. Cl. ............ 435/288.5; 435/287.2; 435/288.3; 435/288.4; 435/288.6; 435/288.7; 435/305.1; 435/305.2; 435/305.3; 422/99; 422/100; 422/104

(58) Field of Classification Search ............... 435/287.2, 435/287.3, 288.3, 288.4, 288.5, 288.6, 288.7, 435/305.1, 305.2, 305.3; 422/99, 100, 104
See application file for complete search history.

(56) References Cited

U.S. PATENT DOCUMENTS 3,799,742 A 3/1974 Coleman (Continued)

FOREIGN PATENT DOCUMENTS

DE 3915920 11/1990

(Continued)

OTHER PUBLICATIONS

A. Guyton, et al., Textbook of Medical Physiology, 4th edition, Chapter 8, pp. 98 and 105 (1971).

(Continued)

*Primary Examiner*—Nathan A Bowers
(74) *Attorney, Agent, or Firm*—Dann, Dorfman, Herrell and Skillman, P.C.; Patrick J. Hagan

(57) ABSTRACT

Disclosed are devices for amplifying a preselected polynucleotide in a sample by conducting a polynucleotide amplification reaction. The devices are provided with a substrate microfabricated to include a polynucleotide amplification reaction, chamber, having at least one cross-sectional dimension of about 0.1 to 1000 μm. The device also includes at least one port in fluid communication with the reaction chamber, for introducing a sample to the chamber, for venting the chamber when necessary, and, optionally, for removing products or waste material from the device. The reaction chamber may be provided with reagents required for amplification of a preselected polynucleotide. The device also may include means for thermally regulating the contents of the reaction chamber, to amplify a preselected polynucleotide. Preferably, the reaction chamber is fabricated with a high surface to volume ratio, to facilitate thermal regulation.

16 Claims, 17 Drawing Sheets

U.S. PATENT DOCUMENTS

| | | | |
|---|---|---|---|
| 4,233,029 | A | 11/1980 | Columbus |
| 4,302,313 | A | 11/1981 | Columbus |
| 4,618,476 | A | 10/1986 | Columbus |
| 4,790,640 | A | 12/1988 | Nason |
| 4,824,247 | A | 4/1989 | True et al. |
| 4,886,761 | A | 12/1989 | Gustafson et al. |
| 4,908,112 | A | 3/1990 | Pace |
| 4,911,782 | A | 3/1990 | Brown |
| 4,963,498 | A | 10/1990 | Hillman et al. |
| 5,135,720 | A | 8/1992 | Uchida |
| 5,147,606 | A | 9/1992 | Charlton et al. |
| 5,176,203 | A | 1/1993 | Larzul |
| 5,188,963 | A | 2/1993 | Stapleton et al. |
| 5,229,297 | A * | 7/1993 | Schnipelsky et al. .......... 436/94 |
| 5,266,272 | A * | 11/1993 | Griner et al. ................ 422/104 |
| 5,270,183 | A | 12/1993 | Corbett et al. |
| 5,296,375 | A | 3/1994 | Kricka et al. |
| 5,304,487 | A | 4/1994 | Wilding et al. |
| 5,346,672 | A | 9/1994 | Stapleton et al. |
| 5,474,796 | A | 12/1995 | Brennan |
| 5,498,392 | A | 3/1996 | Wilding et al. |
| 5,587,128 | A | 12/1996 | Wilding et al. |
| 5,632,957 | A | 5/1997 | Heller et al. |
| 5,639,423 | A | 6/1997 | Northrup et al. |
| 5,955,029 | A | 9/1999 | Wilding et al. |
| 6,660,517 | B1 | 12/2003 | Wilding et al. |

FOREIGN PATENT DOCUMENTS

| | | |
|---|---|---|
| EP | A1318255 B1 | 5/1989 |
| EP | 0 320 308 | 6/1989 |
| EP | 0 483 117 | 8/1990 |
| EP | 0 402 995 | 12/1990 |
| EP | 0 430 248 | 6/1991 |
| EP | 0 439 182 | 7/1991 |
| EP | 0611598 | 8/1994 |
| FR | 2 650 657 | 2/1991 |
| FR | 2650657 | 2/1991 |
| GB | 2191110 | 12/1987 |
| WO | WO 9004645 | 5/1990 |
| WO | 90/09596 | 8/1990 |
| WO | WO 9113338 | 9/1991 |
| WO | 91/15750 | 10/1991 |
| WO | 91/16966 | 11/1991 |
| WO | WO 9313220 | 7/1993 |
| WO | WO 9405414 | 3/1994 |

OTHER PUBLICATIONS

Wilding, et al., Clinical Chemistry, 40: 1815-1818 (1994).
Yap, et al., Nucleic Acid Research, 19: 4294 (1991).
Anderson, "Roche Cuts Controversial PCR Fees, Testing Limits," *Nature*, 355:379 (1992).
Angell, et al., "Silicon Micromechanical Devices," *Scientific American*, 248:44-55 (1983).
Appenzeller et al., "The Man Who Dared to Think Small" and "Engineering a Small World: From Atomic Manipulation to Microfabrication," *Science*, 254:1300-1342 (1991).
Backman, "Ligase Chain Reaction: Diagnostic Technoogy for the 1990's and Beyond," *Clin. Chem.*, 38:457-458 (1992).
Barany, "Genetic Disease Detection and DNA amplification using cloned Thermostable Ligase," *Proc. Natl. Acad. Sci.*, 88:189-193 (1991).
Brown, "Development of a Stopped-Flow Cytometer," NSF Grant No. ISI 87-60730, (1987).
Brunette, "Spreading and Orientation of Epithelial Cells on Grooved Substrata," Exper. Cell Res., 167:203-217 (1986).
Brunette, "Fibroblasts on Micromachined Substrata Orient Hierarchically to Grooves of Different Dimensions," *Exper. Cell Res.*, 164:11-26 (1986).

*Chem. and Eng. News*, "Dye Can be Used to Detect Amplified DNA" Apr. 13, 1992, p. 38.
Chien et al., "Deoxyribonucleic Acid Polymerase from the Extreme Thermophile Thermus Aquaticus," *J. Bacteria.*, 127:1550-1557 (1976).
Columbus et al., "'Architextured' Fluid Management of Biological Liquids," *Clin. Chem.*, 33:1531-1537 (1987).
DeLuca, et al., "Coimmobilized Multiemzymes: An in Vitro Model for Cellular Processes," *Arch. Biochem. Biophys.*, 255:285-292 (1983).
Dessy, "The Microelectronic Chemical Toolbox," *Chemometrics and Intelligent Laboratory Systems*, 8:311 (1990), Abstract.
Erlich, ed., "Principles and Applications for DNA Amplification," *PCR Technology*, Stockton Press, 1989, pp. 32-38.
Engelke et al., "Direct Sequencing of Enzymatically Amplified Human Genomic DNA," *Proc. Natl. Acad. Sci.*, 85:544-548 (1988).
Esashi et al., "Integrated Flow Control Systems Fabricated on a Wafer," *Proceedings, Electrochemical Society Conference, HI* (Oc. 18-23, 1987) Electorchemcal Society, Pennington, N.J., pp. 31-38B, 1987.
Farr et al., "Analysis of RAS Gene Mutations in Actue Myeloid Leukemia by Polyermase Chain Reaction and Oligonucleotide Probes," *Proc. Natl. Acad. Sci.*, 85:1629-1633 (1988).
Fromherz et al., "Core-coat conductor of lipid bilayer and micromachined silicon," *Biochmica et Biophysica Acta*, 1062:103-107 (1991).
Goin et al., "The 'Intelligent Workstation' for Cell-Surface Phenotyping Based on Principles of Pattern Recognition and Image Analysis," *Clin. Chem.*, 32:1655-1659 (1986).
Haller in: *Solid Phase Biochemistry*, W.H. Scouten, Ed., John Wiley, New York, pp. 535-597 (1983).
Hanazato et al., "Multi-Enzyme Electrode Using Hyrdrogen-Ion-Sensitive Field-Effect Transistors," *IEEE Transactions Electron. Devices*; ED 33:47-51 (1986).
Higuchi et al., "Simultaneous Amplification and Detection of Specific DNA Sequences," Biotechnology, 10:413-417 (1992).
Howe et al., "Resonant-Microbridge Vapor Sensor," *IEEE Transactions Electron Devices*, ED33:499-506 (1986).
Hung et al., "Three-Dimensional Uniform in an Oxygenator," *Med. & Biol. Engng.*, 9:237-245 (1971).
Jonsson et al., "Surface Immobilization Techniques in Combination with Ellipsometry," *Methods in Enzymology*, 137:381-389 (1988).
Kawasahi, "Sample Preparation From Blood, Cells; and Other Fluids," in *PCR Protocols*, Innis et al., eds., Academic Press, Inc., 1990, pp. 146-149.
Kennedy et al., "Protein-Protein Coupling Reactions and the Applications of Protein Conjugates," *Clin. Chem. Acta.*, 70:1-31 (1976).
Kenny et al., "Micromachined Silicon Tunnel Sensor For Motion Detection," *Appl. Phys. Lett.*, 58:100-102 (1991).
Kikuchi et al., "Microchannels Made on Silicon Wafer for Measurement of Flow Properties of Blook Cells," *Biorheology*, 26:1055 (1989), Abstract.
Kittilsland et al., "Filter Structure for Sub-Micron Filtration Fabricated in Silicon," *Journal de Physique*, 49(c4):641-644 (1988).
Kittilsland et al., "A Sub-micron Particle Filter in Silicon," *Sensors and Actuators*, A21-A23:904-907 (1990).
Kricka et al., "Liquid Transport in Micron and Submicron Channels," *SPIE*, 1167:159-168 (1989).

Kricka et al., "Variability in the Adsorption Properties of Microtitre Plates Used as Solid Supports in Enzyme Immunoassay," *Clin. Chem.*, 26:741-744 (1980).

LaCelle, "Alterations by Leukocytes of Erythrocyte Flow in Microchannels," *Blood Cells*, 12:179-189 (1986).

Li et al., "Amplification and Analysis of DNA Sequences in Single Human Sperm and Diploid Cells," *Nature*, 335:414-417 (1988).

Mandenius et al., "The Interaction of Proteins and Cells with Affinity Ligands Covelantly Coupled to Silicon Surfaces as Monitored by Elliposmetry," *Anal. Biochem.*, 137:106-114 (1984).

Mandenius et al., "Detection of Biospecific Interactions Using Amplified Ellipsometry," *Anal. Biochem.*, 170:68-72 (1988).

Mandenius et al., "Coupling of Biomolecules to Silicon Surfaces for Use in Ellipsometry and Other Related Techniques," *Methods in Enzymology*, 137:388-394 (1988).

Manz et al., "Micromachining of Monocrystalline Silicon and Glass for Chemical Analysis Systems," *Trends in Anal. Chem.*, 10:144-149 (1991).

Masuda et al., "Novel Method of Cell Fusion in Field Constriction Area in Fluid Integrated Circuit," *Proc. IEEE/IAS Meeting*, pp. 1549-1553 (1987).

McCartney et al., "Comparison of the Degree of Contact Guidance between Tumor Cells and Normal Cells in Vitro," *Cancer Res.*, 41:3046-3051 (1981).

Moghissi et al., "A Composite Picture of the Menstural Cycle," *Am. J. Obstet. Gynecol.*, 114:405-418 (1972).

Nakamura, *Immunochemical Assays and Biosensor Technology for the 1990's*, American Society of Microbiology, Washington D.C., pp. 205-215 (1992).

Nakamura et al., "Immunoassay Method for the Determination of Immunoglobulin G Using Bacterial Magnetic Particles," *Anal. Chem.*, 63:268-272 (1991).

Oste, "Polymerase Chain Reaction," *Bio Techniques*, 6:162-167 (1988).

Ou et al., "DNA Amplification for Direct Detection of HIV-1 in DNA of Peripheral Blood Monomuclear Cells," *Science*, 239:295-297 (1988).

Parce, et al., "Detection of Cell-Affecting Agents with a Silicon Biosensor," *Science*, 24:243-247 (1989).

Rosenberg et al., "Immunogold Staining: Adaptation of a Cell-Labeling System for Analysis of Human Leukocyte Subsets," *Clin. Chem.*, 30:1462-1466 (1984).

Rosenberg et al., "Fc Receptors for IgG on Human Neutrophils: Analysis of Structure and Function by Using Monoclonal Antibody Probes," Clin. Chem., 31:1444-1448 (1985).

Sankolli, et al., "Improvement in the Antibody Binding Characteristics of Microtitre Wells by Pretreatment With Anti-IgG Fc Immunoglobulin," *J. Immun. Methods*, 104:191-194 (1987).

Sato, et al., "Individual and Mass Operation of Biological Cells using Micromechanical Silicon Devices," *Sensors and Actuators*, A21-A23:948-951 (1990).

Shoji, et al., "Prototype Miniature Blood Gas Analyser Fabricated on a Silicon Wafer," *Sensors and Actuators*, 15:101-107 (1988).

Stange et al., "Quantitative Analysis of Immunological Reactions on Silicon Surfaces by Multiple-angle Brewster Angle Reflectometry," *Biomaterials*, 9:3-6 (1988).

Van Lintel, "A Piezoelectric Micropump Based on Micromachining of Silicon," *Sensors and Acutators*, 15:153-167 (1988).

Vener et al., "A Novel Approach to Nonradioactive Hybridization Assay of Nucleic Acids Using Stained Latex Particles," *Anal. Biochem.*, 198:308-311 (1991).

Walker et al., "Isothermal in Vitro Amplification of DNA by a Restriction Enzyme/DNA Polymerase System," *Proc. Natl. Acad. Sci.*, 89:392-396 (1992).

Wallis et al., "Direct-Current Polarization during Field-Assisted Glass-Metal Sealing," *J. Amer. Ceramic Soc.*, 53:563-567 (1970).

Washizu et al., "Handling of Biological Cells Using Fluid Integrated Circuit," *Proceedings IEE/IAS Meeting*, pp. 1735-1740 (1988).

Weissman et al., "Numerical Simulation of Convective Diffusion in Blood Flowing in a Channel with a Steady, Three-Dimensional Velocity Field," *Am. Inst. Chem. Eng. J.*, 17:25-30 (1971).

Wilding, "New approaches to Point-of-Care Testing," *Advanced Hospital Technology Laboratory*, Oct. 1990, pp. 38-42.

Wolf et al., "Rapid hybridization kinetics of DNA Attached to Submicron Latex Particles," *Nucl. Acids Res.*, 15:2911-2927 (1987).

Zemel et al. In: *Fundamentals and Applications of Chemical Sensors*, D. Schuetzle and R. Hammerle, Eds., Washington, D.C., 1986, p. 2-38.

Biotrack, Ciba Corning, May 1989.

Ontrack™, Roche Diagnostic Systems, Sep. 1988.

Kinosita et al., "Dual-View Microscopy With A Single Camera: Real-Time Imaging of Molecular Orientations And Calcium," *J. Cell Biol.*, 115:67-73 (1991) (Abstract).

Hoopman, "Microchanneled Structures," in *Microstructures, Sensors and Actuators*, Cho et al., Eds., The American Society of Mechanical Engineers, 1990.

Pfahler et al., "Liquid Transport in Micron and Submicron Channels," *Scientific American*, 248(4):36-47 (1983).

* cited by examiner

MESOSCALE POLYNUCLEOTIDE AMPLIFICATION DEVICES

REFERENCE TO RELATED APPLICATIONS

This application is a continuation of U.S. application Ser. No. 08/745,771 (filed Nov. 8, 1996) now U.S. Pat. No. 6,660,517, which is a division of U.S. application Ser. No. 08/338,728 (filed Nov. 14, 1994), now U.S. Pat. No. 5,587,128, which is a continuation-in-part of U.S. Ser. No. 08/308,1999 (filed Sep. 19, 1994), now U.S. Pat. No. 5,498,392, which is a continuation of U.S. Ser. No. 07/877,662 (filed May 1, 1992), now abandoned. U.S. application Ser. No. 08/338,728 was filed contemporaneously with commonly-owned U.S. Ser. No. 08/338,369, which is a continuation-in-part of U.S. Ser. Nos. 07/877,702 (filed May 1, 1992), now abandoned, 08/196,021 (filed Feb. 14, 1994), now U.S. Pat. No. 5,635,358 and Ser. No. 08/250,100 (filed May 6, 1994), now abandoned. The disclosures of all of the above-mentioned applications are incorporated herein by reference.

BACKGROUND OF THE INVENTION

This invention relates generally to methods and apparatus for conducting amplification and various analyses of polynucleotides. More particularly, the invention relates to the design and construction of small, typically single-use, modules for use in analyses involving polynucleotide amplification reactions such as the polymerase chain reaction (PCR).

In recent decades, the art has developed a very large number of protocols, test kits, and cartridges for conducting analyses of biological samples for various diagnostic and monitoring purposes. Immunoassays, immunometric assays, agglutination assays and analyses based on polynucleotide amplification assays (such as polymerase chain reaction), or on various ligand-receptor interactions and/or differential migration of species in a complex sample, all have been used to determine the or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101-107 (1988). Sato et al. reported a cell fusion technique using micromechanical silicon devices. Sato et al., *Sensors and Actuators*, A21-A23:948-953 (1990). Ciba Corning Diagnostics Corp. (USA) has manufactured a microprocessor-controlled laser photometer for detecting blood clotting.

Micromachining technology, using, e.g., silicon substrates, has enabled the manufacture of microengineered devices having structural elements with minimal dimensions ranging from tens of microns (the dimensions of biological cells) to nanometers (the dimensions of some biological macromolecules). Angell et al., *Scientific American*, 248:44-55 (1983). Wise et al., *Science*, 254:1335-42 (1991); and Kricka et al., *J. Int. Fed. Clin. Chem.*, 6:54-59 (1994). Most experiments involving structures of this size relate to micromechanics, i.e., mechanical motion and flow properties. The potential capability of these structures has not been exploited fully in the life sciences.

Brunette (*Exper. Cell Res.*, 167:203-217 (1986) and 164:11-26 (1986)) studied the behavior of fibroblasts and epithelial cells in grooves in silicon, titanium-coated polymers and the like. McCartney et al. (*Cancer Res.*, 41:3046-3051 (1981)) examined the behavior of tumor cells in grooved plastic substrates. LaCelle (*Blood Cells*, 12:179-189 (1986)) studied leukocyte and erythrocyte flow in microcapillaries to gain insight into microcirculation. Hung and Weissman reported a study of fluid dynamics in micromachined channels, but did not produce data associated with an analytic device. Hung et al., *Med. and Biol-Engineering*, 9:237-245 (1971); and Weissman et al., Am. Inst. Chem. Eng. J., 17:25-30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.*, 33:1531-1537 (1987). Masuda et al. and Washizu et al. have reported the use of a fluid flow chamber for the manipulation of cells (e.g., cell fusion). Masuda et al., *Proceedings IEEE/IAS Meeting*, pp. 1549-1553 (1987); and Washizu et al., *Proceedings IEEE/IAS Meeting* pp. 1735-1740 (1988). Silicon substrates have been used to develop microdevices for pH measurement and biosensors. McConnell et al., *Science*, 257:1906-12 (1992); and Erickson et al., *Clin. Chem.*, 39:283-7 (1993). However, the potential of using such devices for the analysis of biological fluids heretofore has remained largely unexplored.

Methodologies for using polymerase chain reaction (PCR) to amplify a segment of DNA are well established. (See, e.g., Maniatis et al., *Molecular Cloning: A Laboratory Manual*, Cold Spring Harbor Laboratory Press, 1989, pp. 14.1-14.35.) A PCR amplification reaction can be performed on a DNA template using a thermostable DNA polymerase, e.g., Taq DNA polymerase (Chien et al. *J. Bacterial.*, 127:1550 (1976)), nucleoside triphosphates, and two oligonucleotides with different sequences, complementary to sequences that lie on opposite strands of the template DNA and which flank the segment of DNA that is to be amplified ("primers"). The reaction components are cycled between a higher temperature (e.g., 94° C.) for dehybridizing ("melting") double stranded template, DNA, followed by lower temperatures (e.g., 40-60° C. for annealing of primers and, e.g., 70-75° C. for polymerization). A repeated reaction cycle between dehybridization, annealing and polymerization temperatures provides approximately exponential amplification of the template DNA. For example, up to 1 µg of target DNA up to 2 kb in length can be obtained from 30-35 cycles of amplification with only $10^{-6}$ µg of starting DNA. Machines for performing automated PCR chain reactions using a thermal cycler are available (Perkin Elmer Corp.)

Polynucleotide amplification has been applied to the diagnosis of genetic disorders (Engelke et al., *Proc. Natl. Acad. Sci.*, 85:544 (1988), the detection of nucleic acid sequences of pathogenic organisms in clinical samples (Ou et al., *Science*, 239:295 (1988)), the genetic identification of forensic samples, e.g., sperm (Li et al., Nature, 335:414 (1988)), the analysis of mutations in activated oncogenes (Farr et al., *Proc. Natl. Acad. Sci.*, 85:1629 (1988)) and in many aspects of molecular cloning (Oste, *BioTechniques*, 6:162 (1988)). Polynucleotide amplification assays can be used in a wide range of applications such as the generation of specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing, and the analysis of mutations.

A wide variety of devices and systems has been described in the art for conducting polynucleotide amplification reactions using thermal cycling procedures. Templeton, *Diag. Mol. Path.*, 1:58-72 (1993); Lizardi et. al., *Biotechnology*, 6:1197-1202 (1988); Backman et al., Eur. Patent No. 320308

(1989); and Panaccio et al., *BioTechniques,* 14:238-43 (1993). The devices use a wide variety of design principles for transfer, such as water baths, air baths and dry blocks such as aluminum. Haff et al., *BioTechniques,* 10:102-12 (1991); Findlay et al., *Clin. Chem.,* 39:1927-33 (1993); Wittwer et al., *Nucl. Acids Res.,* 17:4353-7 (1989). PCR reactions in small reaction volumes have been described. Wittwer et al., *Anal. Biochem.,* 186:328-31 (1990); and Wittwer et al., *Clin. Chem.,* 39:804-9 (1993). Polynucleotide amplification micro-devices fabricated from silicon also have been described. Northrup et al., in: *Digest of Technical Papers*: Transducers 1993 (Proc. 7th International Conference on Solid State Sensors and Actuators) Institute of Electrical and Electronic Engineers, New York, N.Y., pp. 924-6; and Northrup et al., PCT WO 94/05414 (1994).

Silica particles have been shown to bind to nucleic acids, and have been used to isolate nucleic acids prior to PCR analysis. Zeillinger et. al., *BioTechniques,* 14:202-3 (1993). While the art has described the use of silicon and other substrates fabricated with microchannels and chambers for use in a variety of analyses, little attention has been focused on methods for the modification of micromachined silicon or other surfaces, to diminish binding or other properties of the surfaces, which can inhibit reactions, such as polynucleotide amplification reactions, conducted in the devices. Northrup et al. describe the chemical silanization of a PCR reaction chamber in a silicon substrate having a depth of 0.5 mm. Northrup et al., in: *Digest of Technical Papers: Transducers* 1993 (Proc. 7th International Conference on Solid State Sensors and Actuators) Institute of Electrical and Electronic Engineers, New York, N.Y., pp. 924-6; and Northrup et al., PCT WO 94/05414 (1994). The reference of Northrup et al., (in: *Digest of Technical Papers: Transducers* 1993), however, discloses that, in the absence of silanization, untreated silicon surfaces of the reaction chambers had no inhibitory effect on the PCR reaction.

There is a need for convenient, rapid systems for polynucleotide amplification analyses, which could be used clinically in a wide range of potential applications in clinical tests such as tests for paternity, and genetic and infectious diseases and a wide variety of other tests in the environmental and life sciences. There is a need for the development of micro-devices fabricated in substrates such as silicon which permit polynucleotide amplification reactions to be conducted in high yields without interfering effects on the reaction caused by the surfaces of the substrate.

An object of the invention is to provide microscale analytical devices with optimal reaction environments for conducting polynucleotide amplification reactions which can be used to detect very low concentrations of a polynucleotide and to produce analytical results rapidly. Another object is to provide easily mass produced, disposable, small (e.g., less than about 1 cc in volume) devices having functional elements capable of rapid, automated polynucleotide amplification analyses of a preselected cell or cell-free sample, in a range of applications. It is a further object of the invention to provide agents for use in microscale reaction chambers fabricated in solid substrates such as silicon, to diminish potential inhibitory effects of the substrate surfaces on a polynucleotide amplification reaction. It is a further object of the invention to provide apparatus for delivering reagents and sample fluids to and from microscale polynucleotide amplification chambers fabricated in solid substrates such as silicon, and to provide apparatus for sealing the reaction chamber during an amplification reaction. It is yet another object of the invention to provide apparatus that can be used to implement a range of rapid clinical tests, e.g., tests for viral or bacterial infection, tests for cell culture contaminants, or tests for the presence of a recombinant DNA or a gene in a cell, and the like.

These and other objects and features of the invention will be apparent from the description, drawings and claims which follow.

SUMMARY OF THE INVENTION

The invention provides a family of small, mass produced, typically one-use devices (sometimes referred to herein as "chips") for conducting a reaction to enable the rapid amplification of a polynucleotide in a sample. In one embodiment, the device comprises a solid substrate that is fabricated to comprise a mesoscale polynucleotide amplification reaction chamber. The device also may include a cover, e.g., a transparent cover, disposed over the substrate, to seal at least a portion of the reaction chamber during an amplification reaction. The device further includes at least one port in fluid communication with the reaction chamber, for introducing a sample into the chamber (sometimes referred to herein as a "sample inlet port" or inlet port"). The device may include one or more flow channels extending from the ports to the reaction chamber, and/or connecting two or more reaction chambers. The device also may include one or more additional ports in fluid communication with the reaction chamber, to serve as access ports, inlet/outlet ports and/or vents. One or more ports and/or flow channels of the device may be fabricated in the cover or in the substrate. In the device, the reaction chamber may be provided with a composition which diminishes inhibition of a polynucleotide amplification reaction by the wall(s) defining the reaction chamber. The device may also include means for thermally cycling the contents of the chamber to permit amplification of a sample polynucleotide.

The term "mesoscale" is used herein with reference to reaction chambers or flow channels, at least one of which has at least one cross-sectional dimension between about 0.1 µm and 1,000 µm. The flow channels leading to the reaction chamber have preferred widths and depths on the order of about 2.0 to 500 µm. Chambers in the substrate wherein amplification takes place may have one or more larger dimensions, e.g., widths and/or lengths of about 1 to 20 mm. Preferred reaction chamber widths and lengths are on the order of about 0.5 to 15 mm. The reaction chambers are fabricated with depths on the order of about 0.1 to at most about 1,000 µm. Typically, the reaction chambers are fabricated with depths less than 500 µm, e.g., less than about 300 µm, and optionally less than about 80 µm. Fabrication of the reaction chamber, with shallow depths, e.g., less than 300 µm, advantageously facilitates heat transfer to the reaction chamber contents, e.g., through the substrate, and permits efficient thermal cycling during an amplification reaction requiring thermal cycling. However, in some embodiments, the reaction chambers may be fabricated with depths between about 500 µm and 1,000 µm. The overall size of the device ranges from microns to a few millimeters in thickness, depending on the material from which it is constructed, and approximately 0.2 to 5.0 centimeters in length or width.

The devices may be used to amplify and/or analyze microvolumes of a sample, introduced into the flow system through an inlet port defined, e.g., by a hole communicating through the substrate or the cover. The volume of the mesoscale flow system typically will be less than 50 µl, and the volume of the reaction chambers is often less than 20 µl, e.g., 10 µl or less. The volume of the individual channels and chambers in another embodiment may be less than 1 µl, e.g., in the nanoliter or picoliter range. Polynucleotides present in very low concentrations, (e.g., nanogram quantities) can be rapidly amplified (e.g., in less than ten minutes) and detected. After a polynucleotide amplification assay is complete, the devices may be discarded or they may be cleaned and re-used.

In one embodiment, reaction chambers may be fabricated wherein the ratio of the surface area of the walls defining the reaction chamber to the volume of the reaction chamber is greater than about 3 mm$^2$/μl. Chambers also may be fabricated with even higher surface area to volume ratios, such as 5 mm$^2$/μl or, optionally, greater than 10 mm$^2$/μl. As the ratio of the surface area to volume increases, heat transfer through the substrate to and from the reaction chamber contents is facilitated, and thus thermal cycling of the reaction becomes more efficient, and the productivity of the reaction is increased. Additionally, however, as the ratio of the surface area to volume increases, potential inhibitory effects of the walls of the substrate on the polynucleotide amplification reaction are increased. Depending on the material from which the device is made, the wall surfaces of the mesoscale channels and chambers could interfere with the polynucleotide amplification, e.g., via binding interactions between the material and sample polynucleotides or amplification reagents.

The invention provides a range of compositions which may be provided in the reaction chamber to diminish the potentially inhibitory effects of the reaction chamber wall surfaces, such as silicon surfaces, on the reaction. The compositions are particularly useful in reaction chambers having a surface area to volume ratio greater than about 3 mm$^2$/μl or 5 mm$^2$/μl, or, in another embodiment, in chambers wherein the ratio exceeds about 10 mm$^2$/μl. The device also may include a cover disposed over the reaction chamber to seal the reaction chamber during an amplification reaction. The cover may comprise a material such as glass or silicon, or a plastic material. The use of a cover disposed over the reaction chamber increases the total amount of surface area in contact with fluid in the reaction chamber. The surface of the cover exposed to the reaction chamber also may be treated with compositions as disclosed herein to reduce potentially inhibitory effects of the cover surface material on the amplication reaction.

A composition provided in the reaction chamber to diminish inhibition of an amplification reaction by a wall of the reaction chamber may be covalently or non-covalently adhered to the surface of the reaction chamber wall, or may be provided in solution in the reaction chamber during an amplification reaction. In one embodiment, the wall surfaces of one or more reaction chamber(s) and/or channel(s) in the device may be coated with a silane, using a silanization reagent such as dimethychlorosilane, dimethydichlorosilane, hexamethyldisilazane or trimethylchlorosilane (available, e.g., from Pierce, Rockford, Ill.). Alternatively, the surface of the walls of the reaction chamber(s) and/or the flow channel(s), e.g., fabricated within a silicon substrate, may be provided with a relatively inert coating, for example, using a siliconizing reagent, such as Aquasil™ or Surfasil™ (Pierce, Rockford, Ill.), or Sigmacote™ (Sigma Chemical Co., St. Louis, Mo.). Siliconizing reagents available from commercial manufacturers, such as Pierce (Rockford, Ill.) or Sigma Chemical Co. (St. Louis, Mo.), are organosilanes containing a hydrolyzable group, which can hydrolyze in solution to form a silanol which can polymerize and form a film over the surface of the chamber, and can react with hydroxyl groups on the surface of the chamber, such that the film is tightly bonded over the entire surface. The coating may further include a macromolecule (sometimes referred to herein as a "blocking agent") noncovalently or covalently associated with the silicone coating, to further reduce inhibitory effects of the wall of the reaction chamber on the amplification reaction. Useful macromolecules include an amino acid polymer, or polymers such as polyvinylpyrrolidone, polyadenylic acid and polymaleimide.

A silicon oxide film may be provided on the surface of the reaction chamber and/or channel walls, in a silicon substrate, to reduce inhibition of the amplification reaction by the wall surfaces. The silicon oxide film may be formed by a thermal process wherein the silicon substrate is heated in the presence of oxygen. Alternatively, a plasma-enhanced oxidation or plasma-enhanced chemical vapor deposition process may be utilized. Additionally the reaction chamber and/or channel walls may be coated with a relatively inert polymer such as a poly (vinyl chloride).

Prior to addition of the sample polynucleotide and amplification reagents to the reaction chamber, another polynucleotide (sometimes referred to herein as a "blocking" polynucleotide) may be added to the chamber, such as genomic DNA or polyadenylic acid, preferably at a concentration greater than the concentration of the sample polynucleotide. This permits the blocking polynucleotide to occupy any sites on the wall surfaces that could potentially bind to the sample polynucleotide and reduce the yield of the reaction or the precision of the assay. Thus, in one-embodiment, a blocking polynucleotide may be provided in a reaction chamber fabricated within a silicon substrate, such that the blocking polynucleotide may occupy any polynucleotide binding sites, such as free hydroxyl groups, on the wall surfaces of the reaction chamber. To avoid interfering with the amplification reaction, the blocking polynucleotide should comprise sequences unrelated to that of the sample polynucleotide. Other compositions which bind to the chamber wall surfaces, such as polyguanylic acid or various polypeptides such as casein or serum albumin, could also be utilized as a blocking agent.

The devices may be utilized to implement a polynucleotide amplification reaction, such as a polymerase chain reaction (PCR), in the reaction chamber. The reaction chamber may be provided with reagents for PCR including a sample polynucleotide, polymerase, nucleoside triphosphates, a first primer hybridizable with the sample polynucleotide, and a second primer hybridizable with a sequence that is complementary to the sample polynucleotide, wherein the first and second primers define the termini of the amplified polynucleotide product. The device also may include means for thermally cycling the contents of the amplification reaction chamber, such that, in each cycle, e.g., the temperature is controlled to 1) dehybridize ("melt") double stranded polynucleotide, 2) anneal the primers to single stranded polynucleotide, and 3) synthesize amplified polynucleotide between the primers. Other amplification methods available in the art also may be utilized, including, but not limited to: (1) target polynucleotide amplification methods such as self-sustained sequence replication (3SR) and strand-displacement amplification (SDA); (2) methods based on amplification of a signal attached to the target DNA, such as "branched chain" DNA amplification (Chiron Corp.); (3) methods based on amplification of probe DNA, such as ligase chain reaction (LCR) and QB replicase amplification (QBR); and (4) various other methods such as ligation activated transcription (LAT), nucleic acid sequence-based amplification (NASBA), repair chain reaction (RCR) and cycling probe reaction (CPR) (for a review of these methods, see pp. 2-7 of *The Genesis Report*, DX, Vol. 3, No. 4, February 1994; Genesis Group, Montclair, N.J.).

The reaction chamber may be fabricated with one section which is thermally cycled sequentially between the required temperatures for polynucleotide amplification reactions requiring thermal cycling, such as conventional PCR. Alternatively, the reaction chamber may comprise two or more sections, set at the different temperatures required for dehybridization, annealing and polymerization, in which case the device further comprises means for transferring the contents of the chamber between the sections to implement the reaction, e.g., a pump controlled by a computer. The reaction chamber may be bound in at least a portion of the chamber by a cover disposed over the substrate. The device may further include means for detecting the amplified polynucleotide, as disclosed herein. The devices may be used to implement a variety of automated, sensitive and rapid polynucleotide analyses, including analyses for the presence of polynucleotides in cells or in solution, or for analyses for a virus or cell types using the presence of a particular polynucleotide as a marker.

The mesoscale flow channel(s) and reaction chamber(s) may be designed and fabricated from solid substrates using established micromachining methods such as photolithography, etching and disposition techniques, laser machining, LIGA processing ('Becker et al., *Microelec. Eng.* 4: 35-56, 1986) and plastic molding. The mesoscale flow systems in the devices may be constructed by fabricating flow channels and one or more reaction chambers into the surface of the substrate, and then adhering or clamping a cover over the surface. The solid substrate and/or cover may comprise a material such as silicon, polysilicon, silica, glass, gallium arsenide, polyimide, silicon nitride and silicon dioxide. The cover and/or the substrate alternatively may comprise a plastic material such as an acrylic, polycarbonate polystyrene or polyethylene. Optionally the cover and/or substrate may comprise a transparent material.

An appliance also may be provided, for use with the device, which contains a nesting site for holding the substrate of the device and which optionally mates one or more input ports on the substrate with one or more flow lines in the appliance. After a biological fluid sample suspected to contain a particular polynucleotide is applied to the inlet port, the substrate is placed in the appliance and pumps, e.g., disposed in the appliance, are actuated to force the sample through the flow system. Alternatively, a sample may be injected into the substrate by the appliance (e.g. by a syringe fitted to the appliance). Reagents required for the assay, such as a polymerase enzyme, may be added (in liquid or in dry form) to the polynucleotide sample prior to injection into the substrate. Alternatively, reagents necessary to complete the assay can be injected into the reaction chamber from a separate inlet port, e.g., by the appliance. Fluid samples and reagents may also enter the mesoscale flow system by capillary action or by gravity.

The invention also provides means for sealing one or more of the fluid inlet/outlet ports in the device during an amplification reaction. This advantageously prevents evaporation of liquids during thermal cycling and thus maintains the preferred reaction concentrations during the amplification reaction. In one embodiment, an apparatus including means for delivering fluid to and from the reaction chamber through a port in the device, and adapted to interfit and/or interlock with the port is provided, which can reversibly seal the port after delivery of fluid to the reaction chamber. For example, the fluid delivery apparatus may comprise a syringe or pipette. In one embodiment, the fluid delivery apparatus may comprise a pipette including a pipette tip provided with an aperture for transferring fluid between the pipette and the port. The pipette tip optionally may be releasable from the pipette, and may be disposable to prevent contamination between samples.

The device may include a substrate comprising a heat conducting material such as silicon, as well as a cover disposed over the substrate, which may comprise a transparent material such as glass or a plastic. The device also includes the mesoscale polynucleotide amplification chamber, fabricated within the substrate or the cover. The cover may include a cavity for receiving and interfitting with the pipette used to deliver sample and reagent solutions to and from the reaction chamber. The device may further include a flow channel that communicates through the substrate and/or the cover between the aperture of the pipette tip and the reaction chamber, when the pipette is fitted within the cavity. The aperture may be positioned on a wall of the pipette tip to permit the pipette tip to move between a first position which permits transfer of fluid from the tip through the aperture and the channel to the reaction chamber, and a second position to permit the aperture to face a wall of the cavity, thereby to seal the flow channel and the reaction chamber during a reaction. Additionally, a depressible member may be provided which extends from the substrate and can seal the port upon depression of the member against the port.

The temperature of one or more section(s) in the reaction chamber can be regulated by, e.g., providing one or more electrical resistance heaters in the substrate near the reaction chamber, or by using a pulsed laser or other source of electromagnetic energy directed to the reaction chamber. The appliance may include electrical contacts in the nesting region which mate with contacts integrated into the structure of the substrate, e.g., to power electrical resistance heating of the reaction chamber. A cooling element may also be provided in the appliance, to assist in the thermal regulation of the reaction chamber. The appliance may be provided with conventional circuitry in communication with sensors in the device for thermally regulating the temperature cycles required for the dehybridization and polymerization reactions.

The amplified polynucleotide produced by the polynucleotide amplification reaction in the mesoscale reaction chamber can be collected through a port in the substrate and detected. Alternatively, specific reagents and methods known in the art may be employed to directly detect amplification products in the reaction chamber ("Taq Man"™ PCR reagents and kit, available from Perkin Elmer Corp., for example). As another alternative, a mesoscale detection region may be microfabricated in the substrate, in fluid communication with the reaction chamber in the device, as a part of the mesoscale flow system. The detection region may include a labeled binding moiety, such as a labeled polynucleotide or antibody probe, capable of detectably binding with the amplified polynucleotide. The presence of polymerized polynucleotide product in the detection region can be detected, e.g., by optical detection of agglutination of the polymerized polynucleotide and the binding moiety through a glass cover over the detection region or through a translucent or transparent section of the substrate itself. Alternatively, the detection region may comprise a series of channels or microlithographic arrays for electrophoretically separating and detecting an amplified polynucleotide.

A positive assay may also be indicated by detectable changes in sample fluid flow properties, such as changes in pressure or electrical conductivity at different points in the flow system upon production of amplified polynucleotide in the reaction chamber. In one embodiment, the device comprises a mesoscale flow system which includes a polynucleotide amplification reaction chamber, and a detection region (e.g., a chamber or a portion of a flow channel), used in combination with an appliance which includes sensing equipment such as a spectrophotometer capable of reading a positive result through an optical window, e.g., disposed over the detection region. The appliance may also be designed to receive electrical signals indicative of a pressure reading, conductivity, or the like, sensed in the reaction chamber, the detection region, or some other region of the flow system.

The substrate may comprise a plurality of reaction and/or detection chambers to enable the rapid parallel amplification and/or detection of several polynucleotides in a mixture. The mesoscale flow system may include protrusions, or a section of reduced cross-sectional area, to cause lysis of cells in the microsample prior to delivery to the reaction chamber. Sharp edged pieces of silicon, trapped in the flow path, can be used as a lysis means. The mesoscale flow system also may include a cell capture region comprising a binding moiety, e.g., immobilized on a wall of a flow channel, which binds a particular type of cell in a heterogeneous cell population at a relatively low fluid flow rate, and at a greater flow rate or by changing the nature of the solvent, for example, releases the cell type prior to delivery of the cells to a cell lysis region, then to a reaction chamber. In this embodiment, intracellular DNA or RNA is isolated from a selected cell subpopulation and delivered to the mesoscale reaction chamber for polynucleotide analysis in one device. In an alternative embodiment, the binding reagent may by immobilized on a solid particle, such as a latex or magnetic bead, as described below.

Complex-forming agents, such as magnetic beads coated with a polynucleotide probe, may be provided within the mesoscale flow system, which can be moved along the flow system by an external magnetic field, e.g., in the appliance. The polynucleotide probe immobilized on the magnetic beads enables the beads to bind to amplified polynucleotide in the reaction chamber or in a separate detection chamber. Magnetic beads containing an immobilized polynucleotide probe may be, e.g., carried through the flow system or otherwise introduced to the reaction chamber at the end of an assay to bind to the amplified polynucleotide product. The bound polynucleotide may then be transported on the magnetic beads to a detection or purification chamber in the flow system, or to a collection port. Alternatively, the magnetic beads may be held in place at a predetermined location in the device, then transported to a detection or purification chamber after binding the polynucleotide product.

Some of the features and benefits of the devices are illustrated in Table 1. The devices can provide a rapid test for the detection of pathogenic bacteria or viruses, or for the presence of certain cell types, or the presence of a gene or a recombinant DNA sequence in a cell. The devices as disclosed herein are all characterized by a mesoscale flow system including a polynucleotide amplification reaction chamber, preferably having at least one mesocale dimension, which is used to amplify a polynucleotide in a sample, and which may be provided with the required amplification reagents. The device may be used to amplify a polynucleotide in a wide range of applications. At the conclusion of the assay the device may be discarded, or it may be cleaned and re-used.

TABLE 1

| Feature | Benefit |
| --- | --- |
| Flexibility | No limits to the number of device designs or applications available. |
| Reproducible | Allows reliable, standardized, mass production of devices. |

TABLE 1-continued

| Feature | Benefit |
| --- | --- |
| Low Cost Production | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Devices can be sterilized for use in microbiological assays and other procedures requiring clean environments. |
| Sealed System | Minimizes biohazards. Ensures process integrity. |
| Multiple Circuit Capabilities | Can perform multiple processes or analyses on a single device. Allows panel assays. |
| Multiple and Detector Capabilities | Expands capabilities for assay process monitoring to virtually any system. Allows broad range of applications. |
| Reusable Devices | Reduces per process cost to the user for certain applications. |

BRIEF DESCRIPTION OF THE DRAWINGS

Like reference characters in the respective drawn figures indicate corresponding parts. The drawings are not necessarily to scale.

DETAILED DESCRIPTION

A. General

Figure 1:
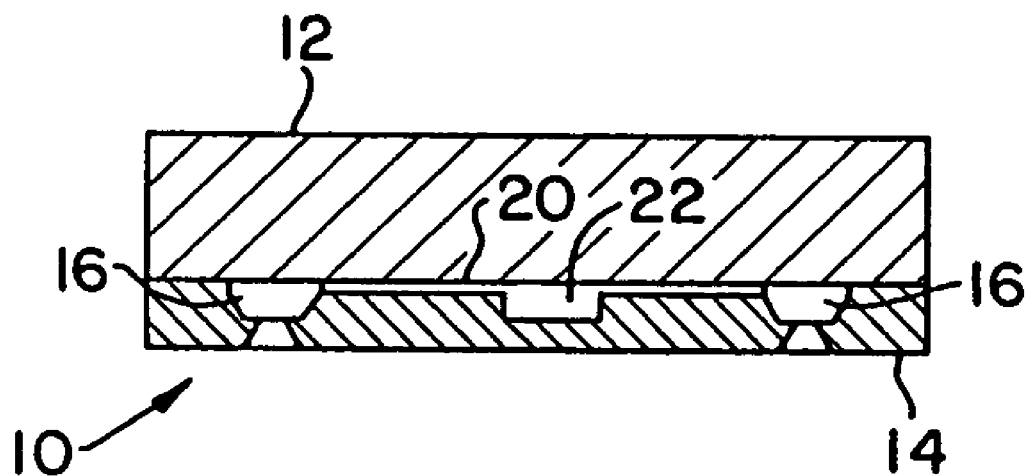
FIG. 1A is a schematic longitudinal cross-sectional view of a device 10 according to the invention that includes a solid substrate 14, on which is machined mesoscale flow channel 20 connected to inlet ports 16 and polynucleotide amplification reaction chamber 22, with a cover 12 adhered to the surface of the substrate.
FIG. 1B is a schematic longitudinal cross-sectional view of an alternative embodiment device 10 according to the invention that includes a solid substrate 14, on which is machined the mesoscale polynucleotide amplification reaction chamber 22 and inlet ports 16, with cover 12 adhered to the surface of the substrate.
FIG. 1C is a schematic longitudinal cross-sectional view of another embodiment of device 10 which includes a solid substrate 14 fabricated with mesoscale polynucleotide amplification reaction chamber 22, and cover 12 fabricated with ports 16 and channels 20 in fluid communication with chamber 22.
Figure 2:
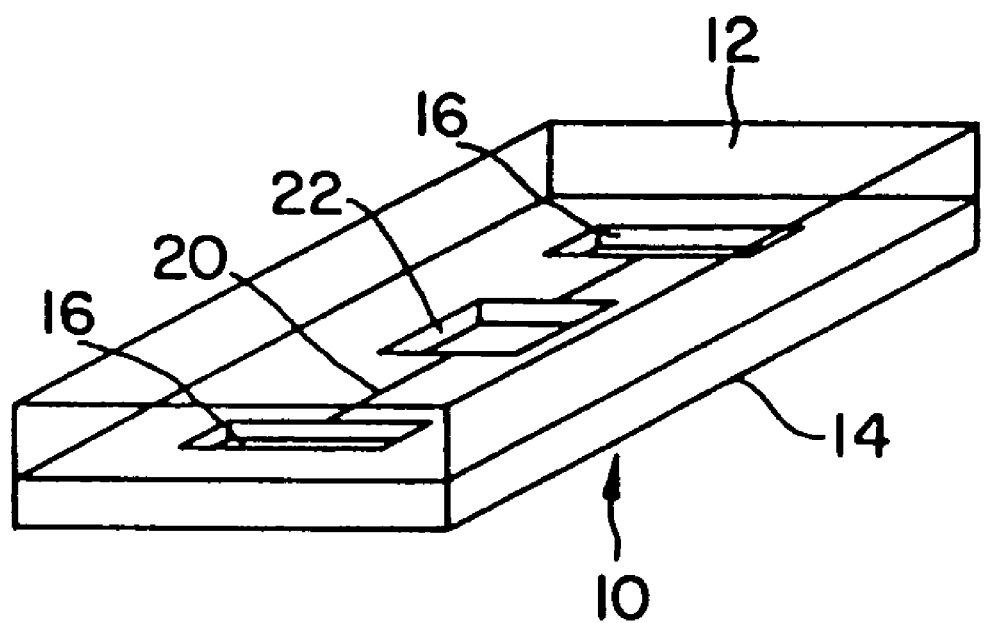
FIG. 2A is a perspective view of the device of FIG. 1A.
FIG. 2B is a perspective view of the device of FIG. 1B.

The invention provides a family of small, mass produced, typically one-use devices for performing polynucleotide amplification reactions to enable the rapid amplification of polynucleotides in fluid samples. The device comprises a solid substrate, fabricated to include at least one polynucleotide amplification reaction chamber, and typically is of a length and/or width ranging from approximately 0.1 to 5.0 centimeters: The channels and chambers in cross-section through the thickness of the device may be triangular, truncated conical, square, rectangular, circular, or any other shape. The device also includes a sample inlet port in fluid communication with the reaction chamber. The device also may include additional ports (which may function as access or inlet/outlet ports, or as vents) disposed at any location over the flow system, and one or more sample flow channels, in fluid communication with the reaction chamber. One or more of the port(s) may be open to the atmosphere or attached to appropriate pressure or suction devices, e.g. for filling or evacuating the device, or they may be sealed, e.g. during an amplification reaction. The port(s) and channel(s) may be fabricated in the substrate or, alternatively, in a cover disposed over the substrate, or both. The device may further include a system for thermally cycling the contents of the reaction chamber to permit amplification of a sample polynucleotide.

At least one of the reaction chambers and the flow channels of the device, and preferably both, have a mesoscale dimension, i.e., at least one cross-sectional dimension on the order of 0.1 to 1,000 µm. The preferred depth of the reaction chamber is less than about 500 µm, more preferably less than 300 µm and most preferably less than 80 µm. The reaction chambers may have larger widths and lengths, e.g., on the order of about 1-20 mm, preferably about 5-15 mm.

The shallow depth of the reaction chamber advantageously facilitates heat transfer to the reaction chamber contents, e.g., from a heater positioned near the substrate, and permits efficient thermal cycling during an amplification reaction. In one embodiment, the reaction chamber may be fabricated such that the ratio of the surface area of the walls of the reaction chamber to the volume of the reaction chamber range from about 3 $mm^2/\mu l$ to greater than about 10 $mm^2/\mu l$. As the ratio of the surface area to volume increases, heat transfer through the substrate and the effectiveness of the thermal cycling of the reaction is improved. However, potential inhibitory effects of the walls of the substrate on the amplification reaction also maybe increased, depending on the material from which the substrate is constructed. Accordingly, compositions are provided which are useful in diminishing inhibitory effects of wall surfaces, such as silicon surfaces, in reaction chambers in which such treatment is warranted.

Compositions provided to diminish inhibition of an amplification reaction by a wall of the reaction chamber may be covalently or non-covalently adhered on the chamber surface. Alternatively, a composition may be provided in solution in the reaction chamber during an amplification reaction. In one embodiment, the mesoscale flow channel(s) and reaction chambers may be fabricated in a silicon substrate. The walls of the reaction chamber(s) and/or channel(s) then may be coated with a composition which reduces inhibition of the reaction by the silicon surfaces in the device. For example, the silicon surfaces of the device may be coated with any of a range of silanizing reagents available in the art as disclosed herein.

In one embodiment, the devices of the invention may be utilized to conduct a polymerase chain reaction (PCR) in the reaction chamber. The chamber is provided with reagents required for a polymerase chain reaction including the sample polynucleotide, a polymerase such as Taq polymerase, nucleoside triphosphates, a first primer hybridizable with the sample polynucleotide, and a second primer hybridizable with a sequence complementary to the polynucleotide, wherein the first and second primers define the termini of the polymerized product polynucleotide. Reagents may be added to a sample and then delivered through an inlet port to the mesoscale reaction chamber, or the reagents may be delivered to the reaction chamber independently of the sample through a separate inlet port.

The polymerase chain reaction may be performed, according to methods established in the art (Maniatis et al., Molecular Cloning: A Laboratory Manual, Cold Spring Harbor Laboratory Press, 1989). Any thermostable polynucleotide polymerase available in the art may be utilized. The device may include means for thermally cycling the contents of the chamber such that, in each cycle, temperature is controlled to dehybridize double stranded polynucleotide to produce single stranded polynucleotide, and then to anneal the primers and enable polynucleotide polymerization.

Although polynucleotide amplification by the polymerase chain reaction has been described and exemplified herein, it will be appreciated by persons skilled in the art that the devices and methods of the present invention may be utilized equally effectively for a variety of other polynucleotide amplification reactions. Such additional reactions may be thermally dependent, such as the polymerase chain reaction, or they may be carried out at a single temperature (e.g., nucleic acid sequenced-based amplification (NASBA)). Moreover, such reactions may employ a wide variety of amplification reagents and enzymes, including DNA ligase, T7 RNA polymerase and/or reverse transcriptase, among others. Additionally, denaturation of polynucleotides can be accomplished by known chemical or physical methods, alone or combined with temperature change. Polynucleotide amplification reactions that may be practiced in the device of the invention include, but are not limited to: (1) target polynucleotide amplification methods such as self-sustained sequence replication (3SR) and strand-displacement amplification (SDA); (2) methods based on amplification of a signal attached to the target polynucleotide, such as "branched chain" DNA amplification (Chiron Corp. Emeryville, Calif.); (3) methods based on amplification of probe DNA, such as ligase chain reaction (LCR) and QB replicase amplification (QBR); (4) transcription-based methods, such as ligation activated transcription (LAT) and nucleic acid sequence-based amplification (NASBA); and (5) various other amplification methods, such as repair chain reaction (RCR) and cycling probe reaction (CPR) (for a summary of these methods and their commercial sources, see pp. 2-7 of *The Genesis Report*, DX, Vol. 3, No. 4, February 1994; Genesis Group, Montclair, N.J.).

The capacity of the devices of the invention is small, enabling assays to be performed on very small amounts of a liquid sample (e.g., less than 50 μl and preferably less that 10 μl). The mesoscale flow systems of the devices may be microfabricated with microliter volumes, or alternatively nanoliter volumes or less, which advantageously limits the amount of sample and/or reagent fluids required for an assay. The devices may be used to implement a variety of automated, sensitive and rapid polynucleotide analyses including the analysis of polynucleotides in cells or in solution. At the conclusion of the assay the devices may be cleaned and re-used, or discarded. The use of disposable devices eliminates contamination and reduces biohazards. The sample and reaction mixture at all times can remain entombed, and the low volume simplifies waste disposal.

B. Substrate Fabrication

Analytical devices comprising a solid substrate and optionally, a cover disposed over the substrate, can be designed and fabricated with mesoscale flow channels and reaction chambers from a wide range of materials. The devices optionally may be fabricated from a material which can be sterilized easily. Silicon provides a useful material because of the well-developed technology permitting its precise and efficient fabrication, but a wide range of other materials may be used within the scope of the invention. Other materials which may be utilized include, e.g., gallium arsenide, indium phosphide, aluminum, polysilicon, silicon nitride, silicon dioxide, polyimide and thermocouple materials such as chrome/aluminum, as well as quartz, glass, diamond, polycarbonate, polystyrene and other polymers such as polytetrafluoroethylenes. Other possible materials include superalloys, zircaloy, steel, gold, silver, copper, tungsten, molybdenum, tantalum, KOVAR, ceramics, KEVLAR, KAPTON, MYLAR, brass, sapphire, or any of a range of plastics and organic polymeric materials available in the art.

The port(s), mesoscale flow system, including sample flow channel(s) and reaction chamber(s), and other functional elements may be fabricated inexpensively in large quantities from, e.g., a silicon substrate by any of a variety of micromachining methods known to those skilled in the art, Micromachining methods available include film deposition processes such as chemical vapor deposition, laser-based fabrication or photolithographic techniques such as UV, X-ray, LIGA processes and plastic molding, or etching methods which may be performed by either wet chemical processes or plasma processes. (See, e.g., Manz et al., *Trends in Analytical Chemistry*, 10:144-149 (1991)). The arrangement of channels, chambers, and multiple ports facilitates the sequential, properly timed, and volumetrically correct addition of sample and reagents within the device.

In one embodiment, flow channels or chambers of varying widths and depths can be fabricated, with at least one having a mesoscale dimension, in a substrate such as silicon. The substrate containing a fabricated mesoscale flow channel and reaction chamber may be covered and sealed with a glass cover clamped, anodically bonded or otherwise adhered to the substrate. Other clear or opaque cover materials may be used. Alternatively, two substrates can be sandwiched, or a substrate can be sandwiched between two glass covers. The use of a transparent cover results in a window which facilitates dynamic viewing of contents in the mesoscale flow system. Other fabrication approaches may be used.

C. Passivation Methods

A composition may be provided in the mesoscale amplification reaction chamber or flow channel to passivate the wall surfaces, i.e., to diminish inhibition of the amplification reaction by the wall surfaces if the nature of the wall material necessitates such treatment. The composition may be adhered to the surface of the reaction chamber or channel walls, either covalently or non-covalently. For example, the wall surfaces may be coated with any of a range of silanization agents known in the art. Alternatively, the composition may be provided in the chamber in solution, together with the sample polynucleotide and the amplification reagent during an analysis. Mesoscale reaction chambers may be fabricated wherein the ratio of the surface area of the wall defining the reaction chamber to the volume of the chamber ranges from about 3 mm$^2$/μl to greater than 10 mm$^2$/μl, or, optionally, greater than 20 mm$^2$/μl. As the surface area to volume ratio increases, heat transfer to the reaction chamber through the substrate is improved, and a thermally dependent amplification reaction may be cycled more rapidly. Concurrently, however, inhibitory effect of the wall surfaces may also be enhanced as the ratio of surface area to volume increases. The compositions for reducing inhibition of the amplication reaction by a wall of the reaction chamber are particularly useful in chambers with a high surface area to volume ratio, e.g., greater than about 3 mm$^2$/μl.

It will be appreciated by those skilled in the art that the passivation compositions and methods described herein are applicable to only certain materials wherein it has been observed that amplification reactions may be improved by passivating reaction chamber surfaces. Some materials contemplated for use in devices of the invention are naturally inert, and so would not benefit from the passivation treatments described herein.

The substrate may comprise a heat conductive material such as silicon or glass. The reaction chamber and/or channel walls may be passivated by coating the surface with a silane using a silanization agent available in the art. Useful silanization agents include dimethylchlorosilane (DMCS), dimethyldichlorosilane (DMDCS), hexamethyldisilazane (HMDS), and trimethylchlorosilane (TMCS). These chlorosilanes can react covalently with surface hydroxyl groups on the walls comprising silicon or another material that potentially could interfere with the reaction by, e.g, binding to the sample polynucleotide or the amplification reagents.

Additionally, the walls of the reaction chambers and/or channels may be provided with a silicone coating using a commercially available siliconizing reagent, such as Aquasil™ or Surfasil™ (Pierce, Rockford, Ill.), or Sigmacote™ (Sigma Chemical Co., St. Louis, Mo.). Siliconizing reagents available from commercial manufacturers, such as Pierce (Rockford, Ill.) or Sigma Chemical Co. (St. Louis, Mo.), are organosilanes containing a hydrolyzable group, which can hydrolyze in solution to form a silanol which can polymerize and form a film over the surface of the chamber, and can react with hydroxyl groups on the surface of the chamber, such that the film is tightly bonded over the entire surface of the chamber.

The coating may further include a macromolecule noncovalently or covalently associated with the coating, to further reduce inhibitory effects of the wall of the reaction chamber on the amplification reaction. Useful macromolecules include an amino acid polymer, or polymers such as polyvinylpyrrolidone, polyadenylic acid, or polymaleimide or compositions such as maleimide. Other useful macromolecules include, e.g., poly-L-alanine, poly-L-aspartic acid, polyglycine, poly-L-phenylalanine, or poly-L-tryptophan. A silicon oxide film may be provided on the reaction chamber and/or channel walls to reduce inhibition of the amplification reaction by silicon wall surfaces. The silicon oxide film may be formed by a thermal process wherein the substrate is heated in the presence of oxygen. Alternatively, a plasma-enhanced oxidation or chemical vapor deposition process may be utilized. Additionally, the reaction chamber and/or channel walls may be coated with polymer, such as poly(vinyl chloride). For example, a solution of poly(vinyl chloride) in chloroform may be added to the mesoscale flow system, and then the coating may be formed upon evaporation of the solvent.

In another embodiment, a blocking agent, such as a polynucleotide or polypeptide, may be added to the chamber. For example, genomic DNA or polyadenylic acid may be added to the solution in the reaction chamber, at a concentration preferably greater than the concentration of the sample polynucleotide. This permits the polynucleotide to occupy any sites on the wall surfaces that potentially could bind to the sample polynucleotide or assay reagents and reduce the yield of the reaction. If DNA or RNA is used as the blocking polynucleotide, it should be effectively devoid of sequences that could interfere with the amplification reaction (i.e., it should contain substantially only sequences unrelated to those of the sample polynucleotide). Other compositions which could be utilized as blocking agents include bovine serum albumin or an amino acid polymer, or polymers such as polyvinylpyrrolidone, or polymaleimide or compositions such as maleimide.

D. Thermal Cycling

Figure 1A:
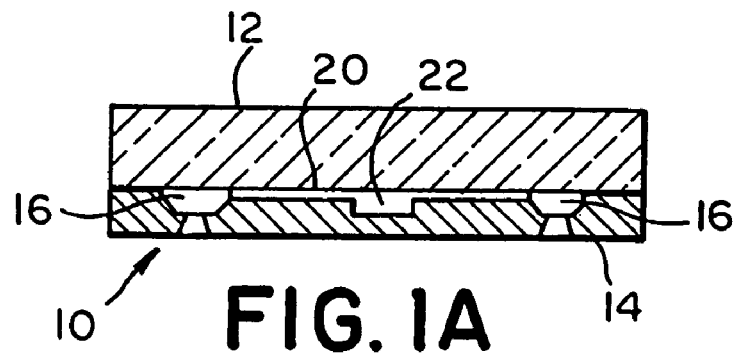
Figure 1C:
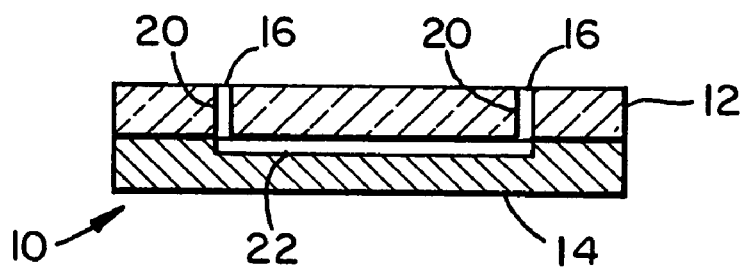
Figure 2A:
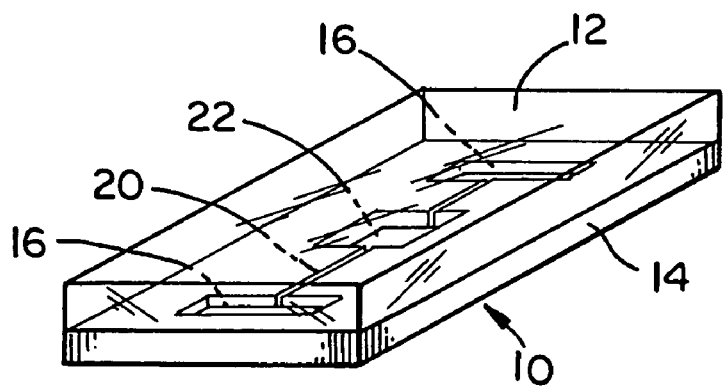
Figure 1B:
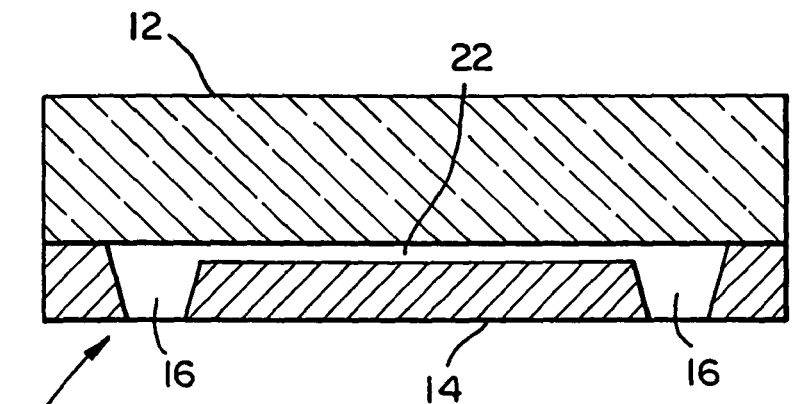
Figure 2B:
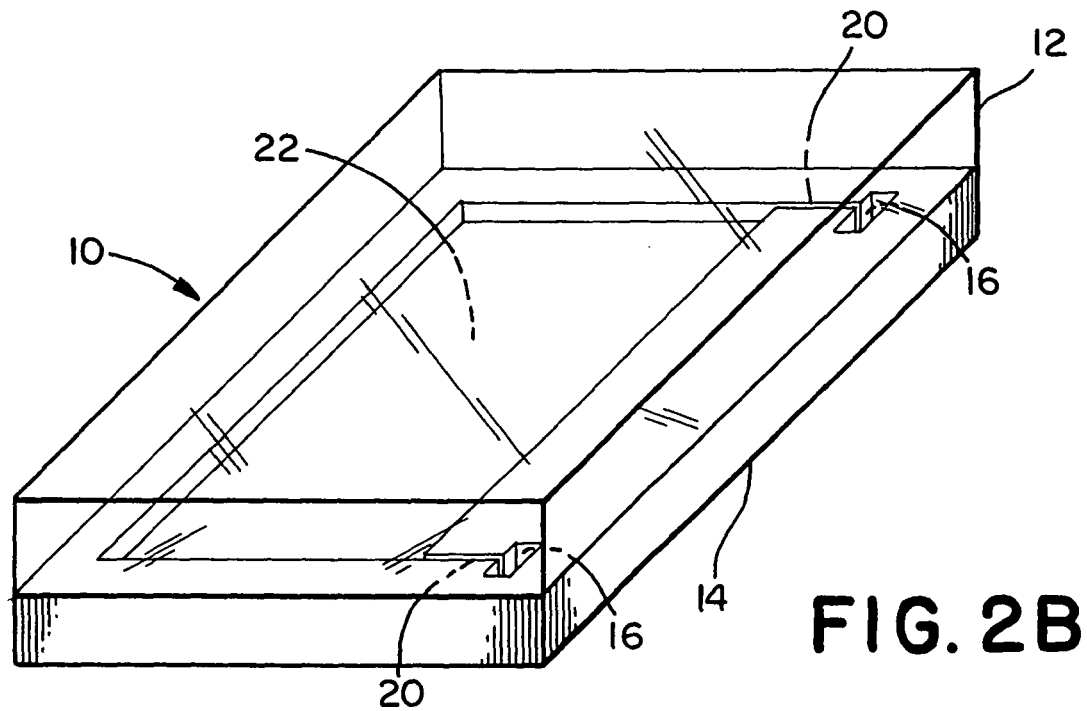
Figure 3A:
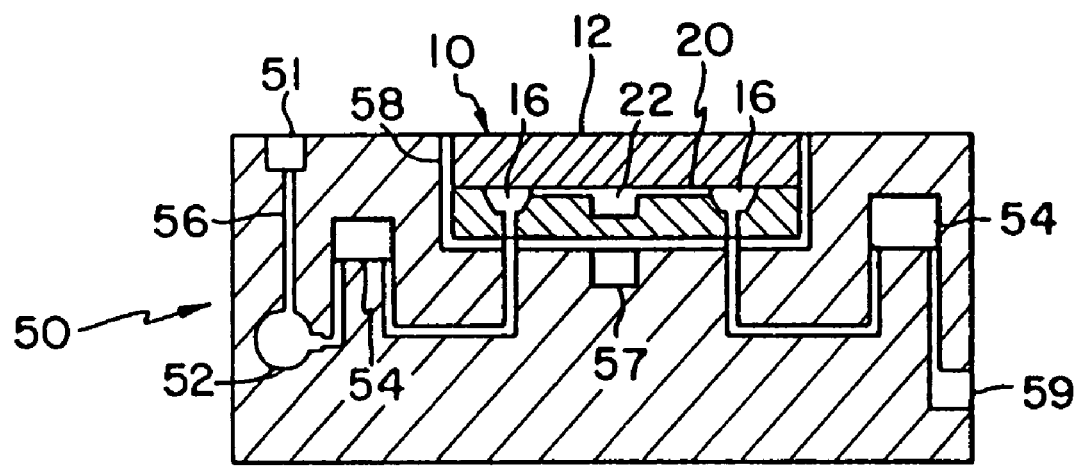
FIG. 3A is a schematic illustration of an analytical device 10 nested within a schematically illustrated appliance 50, which may be used to support the device 10 and which includes heating element 57 for regulating the temperature of the reaction chamber 22 in device 10.

A polynucleotide amplification reaction, such as a PCR reaction, may be conducted in the reaction chamber of the device 10 shown in FIGS. 1A and 2A. An alternative embodiment of device 10 is illustrated in FIGS. 1B and 2B. As illustrated schematically in FIGS. 1A, 1B, 2A and 2B, the device 10 may include a silicon substrate 14 microfabricated with inlet ports 16, a mesoscale flow channel 20, and reaction chamber 22. The polynucleotide sample and the reagents required for the polymerization reaction are added, and the products withdrawn (if necessary) through flow channel 20 from reaction chamber 22 through inlet ports 16 which are fabricated on one end of the flow channel 20. The substrate 14 is covered, e.g., with a glass or plastic cover 12. The device 10 may be used in combination with an appliance, such as appliance 50 shown schematically in FIG. 3A. Appliance 50 includes a nesting site 58 for holding the device 10, and for registering ports, e.g., ports 16 on device 10, with a flow line 56 in the appliance. A pump 52 in appliance 50 is used to deliver a sample and/or reagents from flow line 56 in the appliance to the reaction chamber 22 via the inlet ports 16.

Figure 3B:
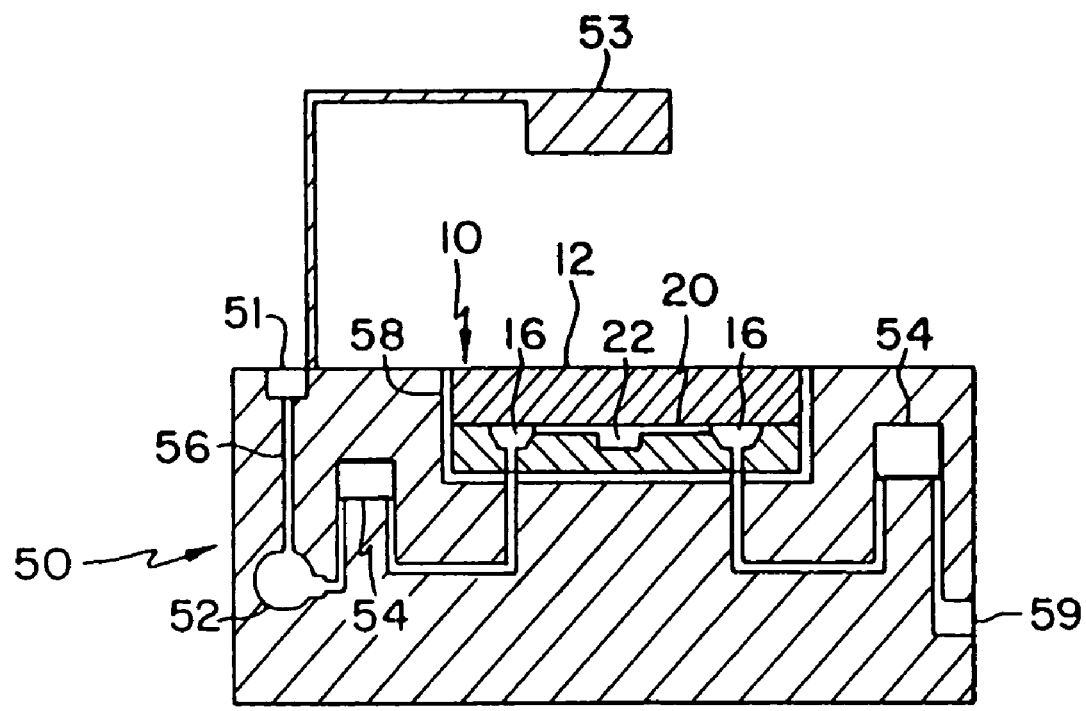
FIG. 3B is a schematic illustration of an analytical device 10 nested within appliance 50, which may be used to support the device 10 and which includes the heating element 53 for regulating the temperature of the reaction chamber 22 in device 10.

The appliance 50 may include a heating/cooling element 57 for controlling the temperature within the PCR chamber, e.g., an electrical heating element and/or a refrigeration coil. The electrical heating element may alternatively be integrated into the substrate 10, with contacts for power mated to matching electrical contacts in the appliance below the reaction chamber 22. Alternatively, as shown in FIG. 3B, the appliance may include a heating means 53, such as a laser, a Peltier heater, or a source of electromagnetic energy, disposed over or adjacent to the reaction chamber in device 10. The heater also may be disposed in the appliance below the reaction chamber. A microprocessor in the appliance may be used to regulate the heating element in order to provide a temperature cycle in the amplification chamber between a temperature suitable for dehybridization, e.g., 94° C., and a temperature suitable for annealing and polymerization, e.g., 40-60° C. for annealing and 70-75° C. for polymerization. A thermocouple, thermistor or resistance thermometer may also be provided in the substrate in electrical contact with the appliance, to allow the microprocessor to detect and maintain the temperature cycles in the reaction chamber. Heating and sensing can advantageously be combined by using a single element, e.g. resistance thermometer, for both purposes, combining heating and sensing either simultaneously or on a multiplexed basis.

A cooling element, such as a miniature thermoelectric heat pump (Materials Electronic Products Corporation, Trenton, N.J.), Peltier thermocouple or Joule Thompson cooling device, may also be included in the appliance for adjusting the temperature of the reaction chamber. In another embodiment, in the appliance shown in FIG. 3B, the temperature of the reaction chamber can be regulated by a timed laser pulse directed at the reaction chamber through glass cover 12, so as to allow sequential heating and cooling of the sample to the required temperatures for the polynucleotide amplification cycle. Additionally, heating and cooling can be advantageously combined by the use of Peltier thermocouples to provide both these functions. The thermal properties of silicon enable a rapid heating and cooling cycle. The use of reaction chambers fabricated with a high surface area to volume ratio, e.g., greater than 3 mm$^2$/μl, is advantageous, since heat transfer to and from the reaction chamber contents is facilitated. This enhances the efficiency of thermal cycling and the productivity of the amplification reaction within the chamber.

Figure 4:
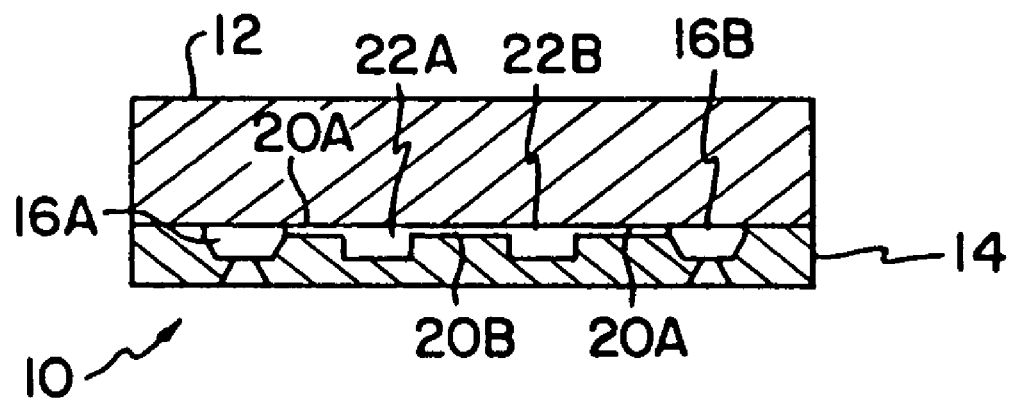
FIG. 4 is a schematic longitudinal cross-sectional view of a device according to the invention that includes a solid substrate 14, on which is machined mesoscale flow channel 20 connected to inlet ports 16 and reaction chamber sections 22, with a cover 12 adhered to the surface of the substrate.
Figure 5:
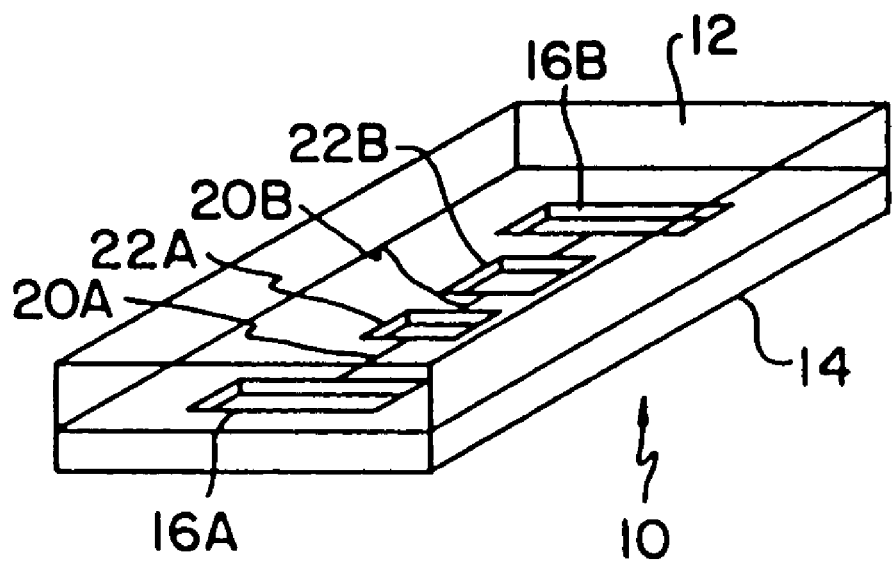
FIG. 5 is a perspective view of the device of FIG. 4.
Figure 6A:
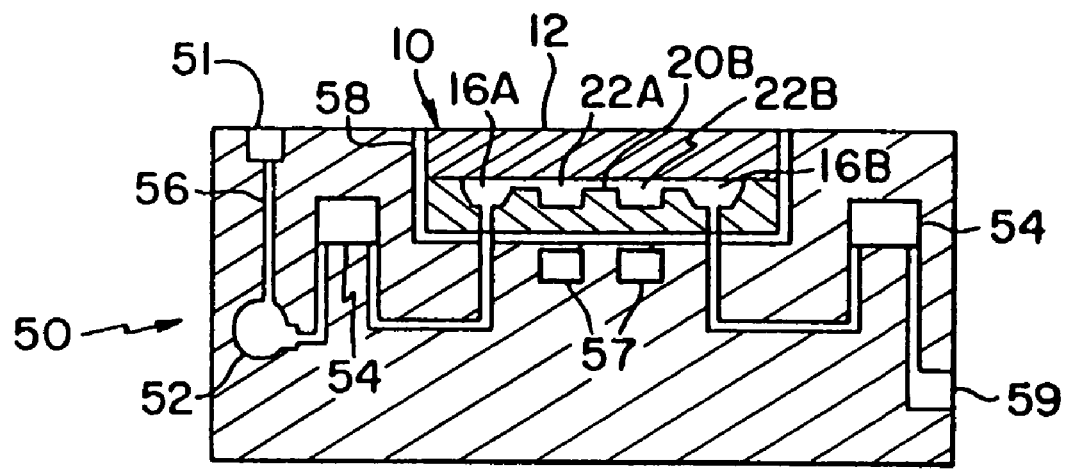
FIG. 6A is a schematic illustration of analytical device 10 nested within appliance 50, which may be used to support the device 10, and which includes heating elements 57 for regulating the temperature of the reaction chamber sections 22 in device 10.

As illustrated schematically in FIGS. 4, 5 and 6A, a mesoscale polynucleotide amplification reaction chamber may be microfabricated with multiple sections, e.g., two sections 22A and 22B, connected by flow channel 20B. In this embodiment, section 22A is heated to or maintained at a temperature suitable for dehybridization and section 22B is heated to or maintained at a temperature suitable for annealing and polymerization. During an analysis, the device 10 may be placed in appliance 50 (FIG. 6A). The appliance 50 is provided with means 57 for controlling the temperature of the reaction chamber sections. Alternatively, a laser may be used to heat the sections. A thermocouple or other temperature sensing device can be included in the substrate to monitor the temperatures of the sections of the reaction chamber, and its output may be used to control thermal input, e.g., with the aid of a microprocessor.

In operation, a pump 52 in the appliance is used to deliver the polynucleotide sample and the required reagents from flow line 56 through inlet port 16A to section 22A. The pump 52, which also may be controlled by a microprocessor in the appliance, is then used to transfer the sample periodically, between sections 22A and 22B, through channel 20B to implement a repetitive polynucleotide amplification reaction cycle, while port 16B serves as a vent. When the reaction is complete, the pump 52 in appliance 50 may be used to deliver the sample through port 16B and line 56 in the appliance to port 59 to recover the product. Of course, three or more chambers may be used, each of which is maintained at a temperature suitable for conducting a particular reaction.

Figure 6B:
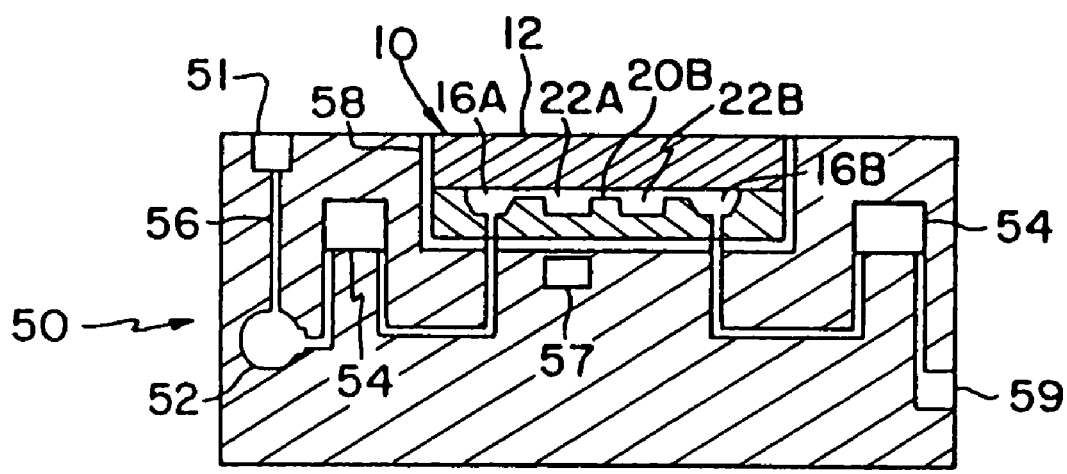
FIG. 6B is a schematic illustration of analytical device 10 nested within appliance 50, which may be used to support the device 10 and which includes heating element 57 for regulating the temperature of the reaction chamber section 22A in device 10.

In the device 10 shown in FIGS. 4, 5 and 6B, a heating element may be used to heat section 22A to a temperature suitable for dehybridization of double stranded DNA, e.g., 94° C., while section 22B and channel 20B, which connects sections 22A and 22B, are spaced apart from section 22A such that upon transport of a heated sample from section 22A to section 22B, heat is dissipated sufficiently to permit the temperature of the sample to fall to the temperature required for annealing and polymerization before the sample is returned to section 22A for further cycling. This may be achieved readily as silicon has a relatively high thermal conductivity and the area of interface between the liquid sample and the substrate is quite high. In this embodiment, microprocessors in the appliance 50 are used to control pump 52, which regulates the flow cycle of the sample between sections 22A and 22B. Thus, a dynamic thermal equilibrium creates a temperature gradient along the flow path between the chambers, and appropriate temperatures are achieved in both using a single heating source. Other designs are possible. For example, the annealing and polymerization reactions could be implemented in different sections of a single chamber, set at different optimized temperatures.

E. Sealing Fluid Transfer Ports

The devices include a solid substrate fabricated with a mesoscale polynucleotide amplification chamber. The devices further include at least one sample inlet port, and a sample flow channel connecting the inlet port to the reaction chamber. One or more ports and flow channels in the device may be fabricated within the substrate (FIG. 1A) or in a cover disposed over the substrate (FIG. 1C). The cover may comprise, e.g., a transparent material, such as glass or any of a range of plastic materials available in the art.

The invention provides means for sealing one or more of the ports during an amplification reaction, to prevent evaporation of liquids during thermal cycling. In one embodiment, a fluid delivery apparatus is provided for delivering fluid to and from the reaction chamber through the port, which is adapted to interfit with and/or interlock with the port, and which can reversibly seal the port after delivery of fluid to the reaction chamber. A syringe or pipette capable of interfitting with and sealing a fluid entry/exit port in the substrate may be utilized.

Figure 19:
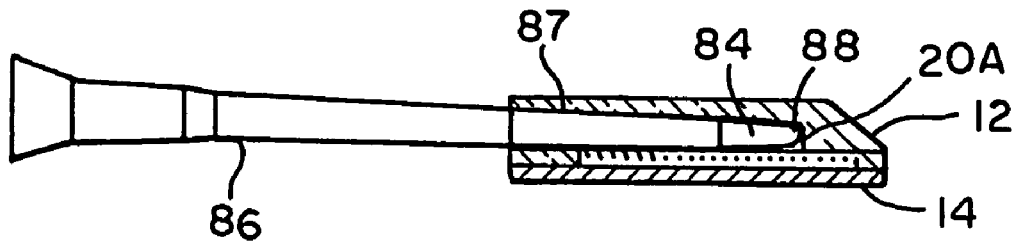
FIG. 19 is a schematic cross-sectional view of a device including substrate 14 and transparent cover 12 which includes cavity 87 receiving pipette 86.
Figure 22:
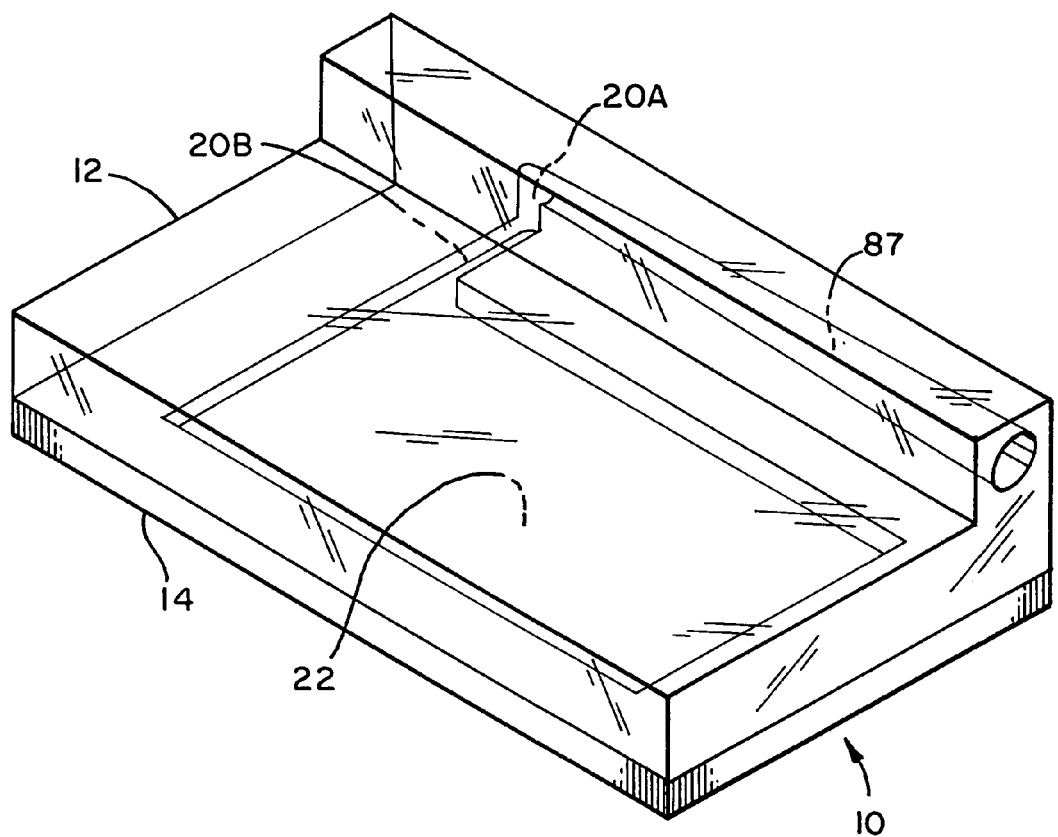
FIG. 22 is a schematic perspective view of an apparatus including transparent cover 12 provided with cavity 87 and flow passage 20A leading to flow channel 20B and reaction chamber 22 in substrate 14.

As illustrated in FIGS. 19 and 22, in one embodiment, cover 12 may be fabricated with cavity 87 for interfitting with and receiving a pipette 86. Pipette 86 may be provided with a pipette tip 84 which includes an aperture 88 for transferring fluid from the pipette tip 84 through flow channel 20A in the cover to flow channel 20B and amplification reaction chamber 22 in substrate 14, when the pipette is interfitted in the cavity 87. The pipette tip optionally may be releasable from the pipette, and may be disposable to prevent contamination between samples.

Figure 20:
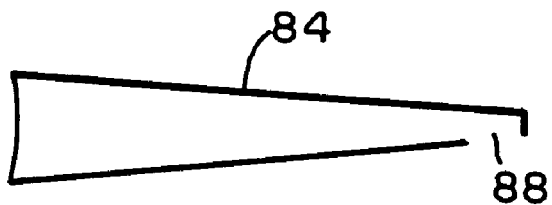
FIG. 20 is a schematic cross-sectional view of a pipette tip 84 including aperture 88.
Figure 21:
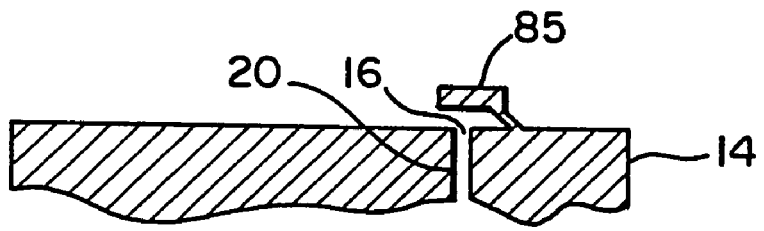
FIG. 21 is a schematic cross-sectional view of a substrate 14 provided with, member 85 which may be compressed to seal port 16 and channel 20.

As illustrated in FIG. 20, the aperture 88 may be positioned on a side wall of pipette tip 84, to permit the pipette tip, on a pipette interfitted in cavity 87 in device 10 shown in FIG. 22, to move between a first position which permits transfer of fluid from the tip through the aperture 88 to the flow channel 20A and to the reaction chamber 22, and a second position to permit the aperture to face a wall of the cavity 87, thereby to seal the channel 20A and the chamber 22 during a reaction. Additionally, a depressible member 85 may be provided, which extends from the substrate, and which is capable of sealing the port upon depression of the member 85, as illustrated in FIG. 21.

Devices comprising sealed fluid transfer ports as described above may be utilized for a variety of purposes other than polynucleotide amplification. For example, such ports may be employed in a separate device for sample preparation, immunoassay, or both, as described in commonly owned co-pending Application Serial No. [not yet assigned] the disclosure of which has been incorporated herein by reference.

F. Detection of Amplified Polynucleotide

Amplified polynucleotide present in the reaction chamber may be detected by a range of methods known in the art for detecting polynucleotides, such as electrophoresis in an agarose gel in the presence of ethidium bromide. In one embodiment, the amplified polynucleotide product may be detected directly in the reaction chamber, using commercially available reagents developed for that purpose (e.g., "Taq Man"™ reagents, Perkin Elmer Corporation). The devices also may be provided with a means for detecting amplified polynucleotide disposed either in the substrate or in an appliance used in combination with the substrate. The presence of amplified polynucleotide product in the device can be detected by any of a number of methods including, but not limited to: (1) monitoring the pressure or electrical conductivity of sample fluids entering and/or exiting the reaction chamber in the mesoscale flow system; (2) forming a detectable complex by, e.g., binding the polynucleotide product with a labeled probe, such as a labeled oligonucleotide or antibody probe; and (3) electrophoretically separating the polynucleotide product from reactants and other components of the sample.

Figure 18:
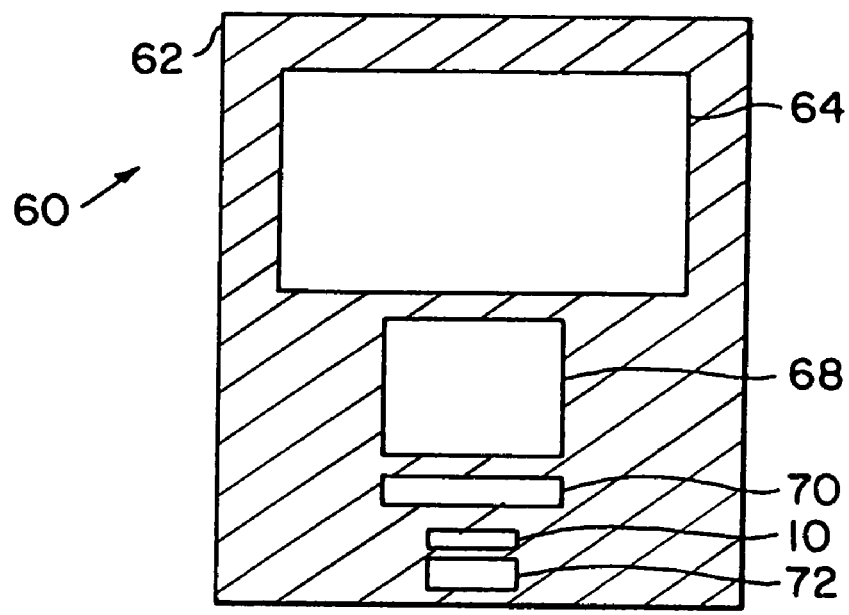
FIG. 18 is a schematic cross-sectional view of the apparatus 60 of FIG. 17.
Figure 17:
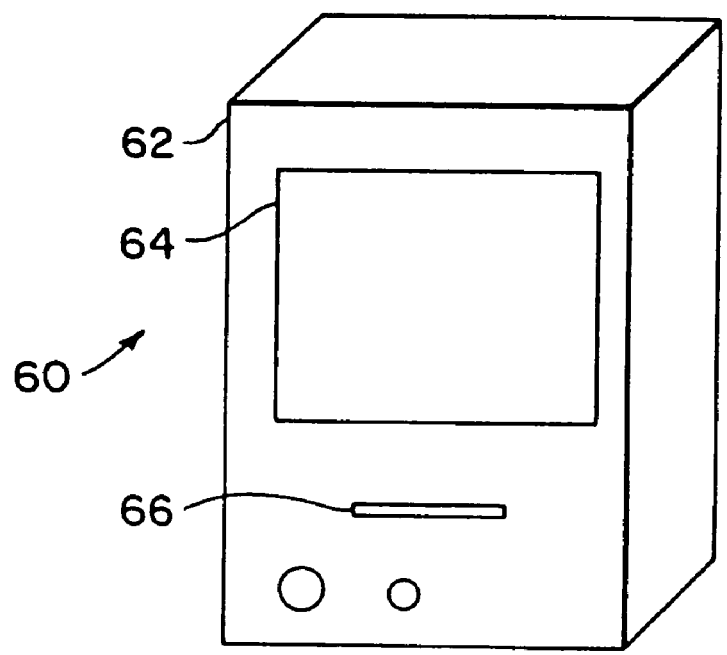
FIG. 17 is a schematic perspective view of an apparatus 60 used in combination with device 10 (not shown) for viewing the contents of device 10.

The analytical devices also may be utilized in combination with an appliance for viewing the contents of the mesoscale channels in the devices. The appliance in one embodiment may comprise a microscope for viewing the contents of the mesoscale channels in the devices. In another embodiment, a camera may be included in the appliance, as illustrated in the appliance 60 shown schematically in FIGS. 17 and 18. The appliance 60 is provided with a housing 62, a viewing screen 64 and a slot 66 for inserting a device into the appliance. As shown in cross section in FIG. 18, the appliance 60 also includes a video camera 68, an optical system 70, and a tilt mechanism 72 for holding device 10, and allowing the placement and angle of device 10 to be adjusted manually. The optical system 70 may include a lens system for magnifying the channel contents, as well as a light source. The video camera 68 and screen 64 allow changes in sample fluid properties, such as flow properties or color, induced by the presence of polynucleotide amplification product, to be monitored visually and optionally recorded using the appliance. Additionally, addition or removal of fluid samples to and from the reaction chambers may be monitored, e.g., optically, using the appliance.

In one embodiment, the amplified polynucleotide product can be detected by using a detection chamber fabricated in the mesoscale flow system in the substrate in fluid communication with the reaction chamber. The detection chamber is provided with a complex-forming agent e.g., a binding moiety capable of binding to the amplified polynucleotide to form a detectable complex. The binding moiety may comprise, e.g., a polynucleotide or antibody probe. The detection chamber may be fabricated in accordance with methods disclosed in U.S. Ser. No. 07/877,702, filed May 1, 1992, the disclosure of which is incorporated herein by reference. In another embodiment, the complex-forming agent may be added to the reaction chamber after the reaction is complete, to form a detectable complex in that chamber. The device may be used in combination with a detector such as an appliance containing a microprocessor for detecting and recording data obtained during an assay.

In one embodiment, the mesoscale detection chamber may be provided with an inert substrate, e.g., a bead or other particle, capable of binding to the polynucleotide product, to cause detectable agglomeration of the beads in the presence of polymerized polynucleotide product. Particle induced agglomeration can be enhanced by the attachment of a binding moiety, such as an antibody, to the particle.

Antibodies or other binding moieties capable of binding to the polynucleotide product may be introduced into the detection chamber, or may be coated, either chemically or by adsorption, onto the surface of the detection region, or alternatively, onto the surface of an inert particle in the detection region, to induce binding, giving a positive test for the polynucleotide. Techniques for the chemical activation of silaceous surfaces are well developed, particularly in the context of chromatography. (See, e.g., Haller in: *Solid Phase Biochemistry*, W. H. Scouten, Ed., John Wiley, New York, pp 535-597 (1983); and Mandenius et al., *Anal. Biochem.* 170: 68-72 (1988)). In one embodiment, the binding moiety may comprise an antibody, and immunoassay techniques known in the art can be performed in the detection region. (See, e.g., Bolton et al., *Handbook of Experimental Immunology*, Weir D. M., Ed., Blackwell Scientific Publications, Oxford, 1986, Vol. 1, Chapter 26, for a general discussion of immunoassays).

An optically detectable label such as a fluorescent molecule or fluorescent bead may be attached to the binding moiety to enhance detection of the amplified polynucleotide product. Alternatively a second labeled substance, such as a fluorescent labeled antibody may be delivered through the flow system to bind to the bound polynucleotide/binding moiety complex in the detection region to produce a "sandwich" including an optically detectable moiety indicative of the presence of the analyte. The binding of the amplified polynucleotide to the binding moiety in the detection region may be detected, e.g., optically, either visually or by machine, through a transparent window disposed over the detection region. In one embodiment, the production of amplified polynucleotide may be detected by the addition of a dye such as ethidium bromide, which exhibits enhanced fluorescence upon binding to double stranded polynucleotide. Higuchi et al., *Biotechnology*, 10:413 (1992).

The detection chamber may also be provided with a labeled complementary polynucleotide capable of binding to one of the strands of the amplified polynucleotide, e.g., a labeled polynucleotide immobilized on a bead, to enable the detection of amplified polynucleotide product by means of bead agglutination. Polynucleotide hybridization techniques known in the art may be utilized. Maniatis et al., *Molecular Cloning: A Laboratory Manual*, 2nd ed., Cold Spring Harbor Press, 1989); Vener et al., *Anal. Chem.*, 198:308-311 (1991). Polynucleotide probes may be attached to, e.g., a submicron latex particle. Wolf et al., *Nucleic Acids Research*, 15:2911-2926 (1987).

In another embodiment, polynucleotide amplification products may be separated from reactants and other components of the original, sample by electrophoretic methods adaptable to the mesoscale devices of the invention. Such techniques are known in the art. For example, microlithographic arrays have been fabricated in $SiO_2$ for the purpose of electrophoretically separating DNA molecules (Volkmuth & Austin, *Nature* 358: 600-602, 1992). Additionally, glass chips have been microfabricated with various combinations of channels for performing capillary electrophoresis to separate various biological molecules (Harrison et al., *Science* 261: 895-897, 1993).

In this embodiment, devices of the invention may be fabricated with a detection region comprising a microlithographic array or series of channels, and electrophoresis may be performed on the chip by providing an appropriate electric field across the region (e.g., by placing microelectrodes at either end of the detection region). The region is provided at one end with a loading area for collecting the contents of the reaction chamber prior to electrophoresis. The various components of the reaction mixture are then separated from one another by electrophoresis. The polynucleotide amplification product may be identified by size comparison with molecules of known size. In one embodiment, size markers are introduced to the detection region (by way of an access port), electrophoretically separated, and the results recorded and stored (e.g. in computer memory). The contents of the reaction chamber are then transferred to the detection region, electrophoretically separated, and the results recorded and compared with the results from electrophoresis of the size markers. In this manner, a polynucleotide amplification product may be identified, as well as being purified for later use, without the use of inert substances and binding moieties for capturing the polynucleotide product.

Polynucleotide amplification also can be detected using a detection region sensitive to flow restriction caused by the presence of polynucleotide produced in the reaction chamber, as is disclosed in U.S. application Ser. No. 08/250,100, the disclosure of which has been incorporated herein by reference. The presence of amplified polynucleotide also may be detected by sensing the pressure or electrical conductivity of the fluid samples entering and exiting the flow system. The conductivity may be measured, e.g., using electrical contacts which extend through the substrate and which mate with electrical contacts in an appliance used in combination with the device. Electrical contacts can be fabricated by known techniques, such as various methods of thermal gradient zone melting. (See Zemel et al., in: *Fundamentals and Applications of Chemical Sensors*, D. Schuetzle and R. Hammerle, Eds., ACS Symposium Series 309, Washington, D.C., 1986, p. 2.)

Amplified polynucleotide in the reaction chamber can be detected by monitoring the pressure of the sample fluids. For example, in a device 10, nested in appliance 50, illustrated schematically in FIG. 6A, the pressure detectors 54 connected to sample fluid entering and exiting the mesoscale flow system through ports 16 will allow the detection of pressure decreases caused by the presence of polymerized product and resulting clogging or flow restriction. A mesoscale pressure sensor also may be fabricated directly on the silicon substrate. Angell et al., *Scientific American* 248: 44-55 (1983).

Polynucleotide amplification can be detected by the use of a mesoscale flow system sensitive to flow restriction, constructed with a "fractal" pattern, i.e., a pattern of diverging flow channels. The channels may be fabricated on a silicon substrate to have progressively reduced dimensions, providing progressively narrower flow channels. It will be appreciated by those skilled in the art that, although bifurcating channels are exemplified, devices may be fabricated with different numbers of parallel flow channels or other symmetrical or asymmetrical patterns of flow channels with reduced cross-sectional areas. Alternatively, a single channel comprising a narrowed region may be utilized, as described in commonly-owned U.S. application Ser. No. 08/250,100 (incorporated by reference herein).

Figure 7:
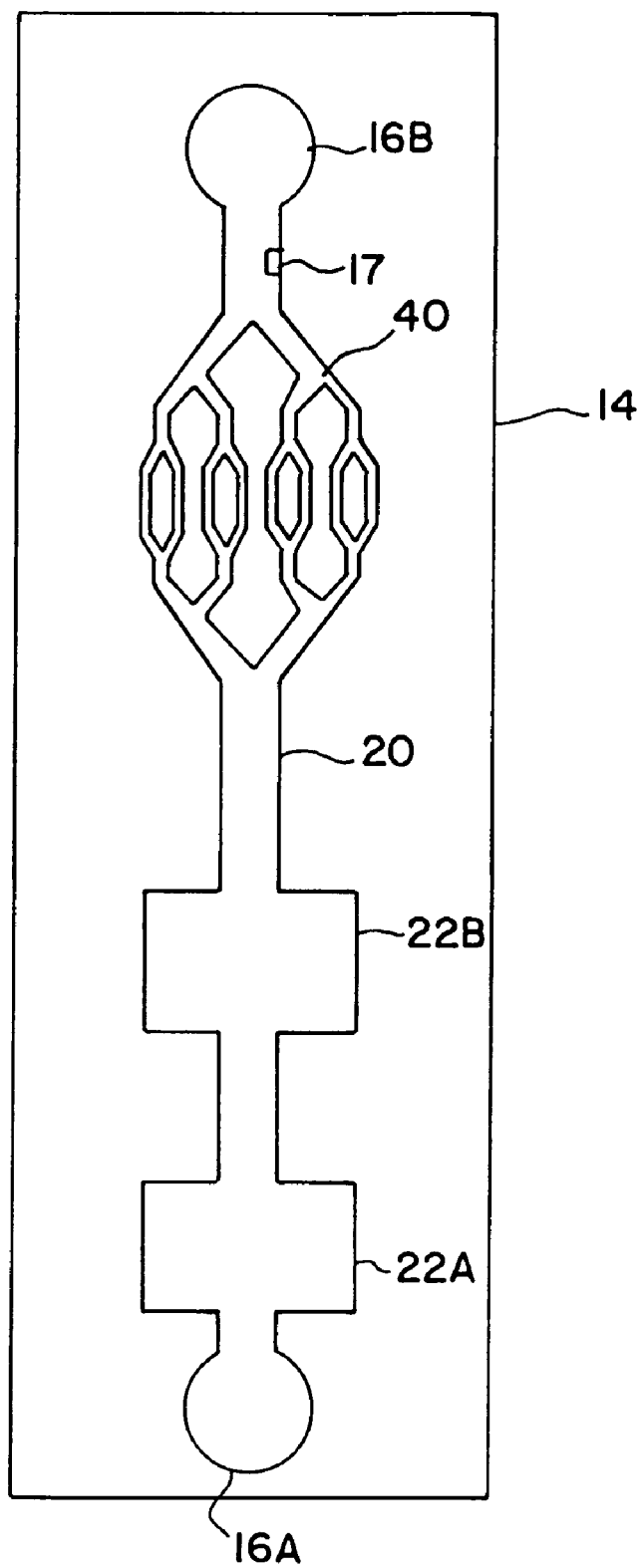
FIG. 7 is a schematic plan view of a substrate 14 microfabricated with mesoscale reaction chamber sections 22A and 22B, in fluid communication with a detection chamber comprised of a diverging system of flow channels 40 of progressively decreasing cross-sectional dimension disposed on the substrate.
Figure 13:
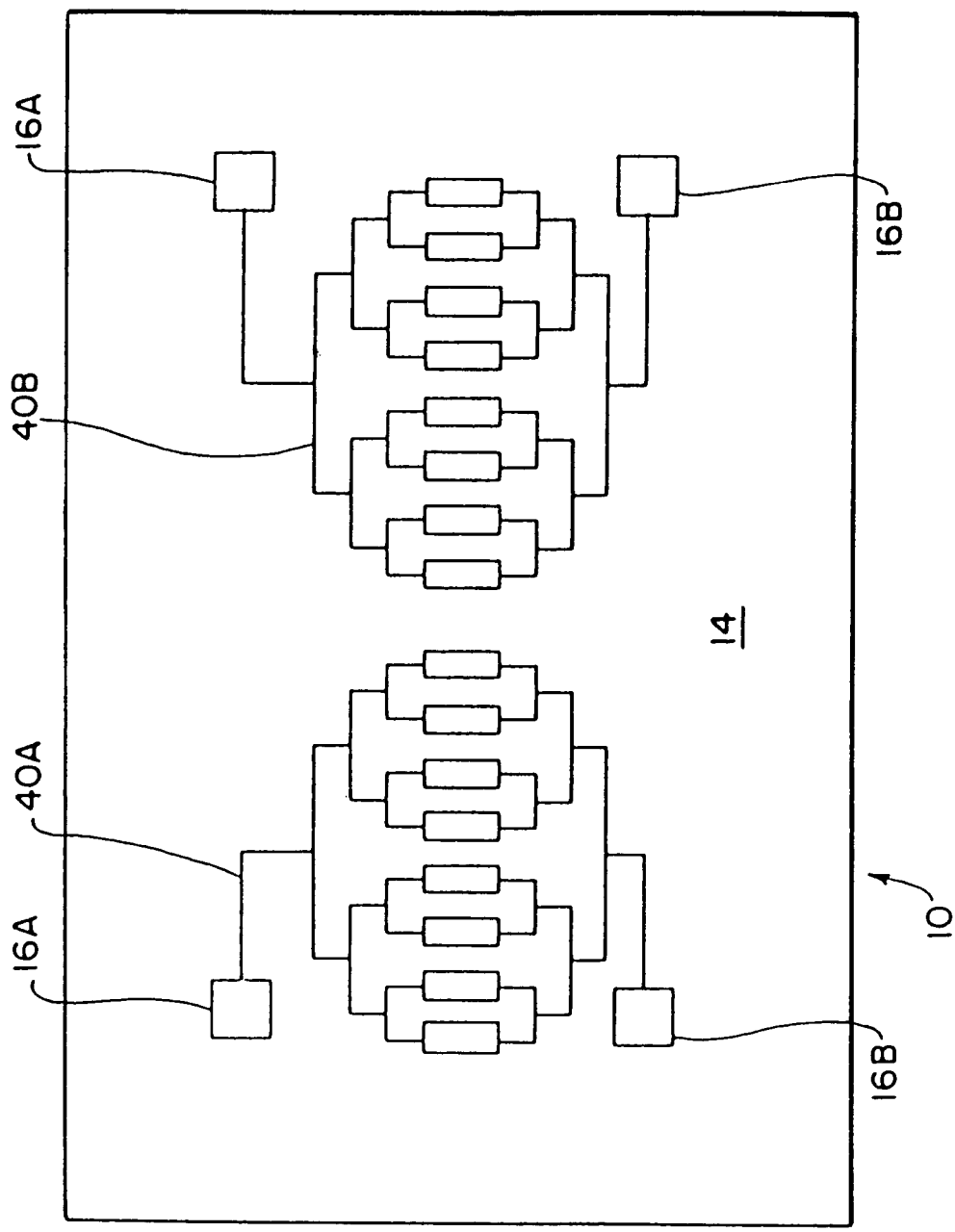
FIG. 13 is a schematic plan view of an analytical device fabricated with two systems of split flow channels 40.

FIG. 7 shows a schematic plan view of a substrate 14 fabricated with a system of flow channels 40 connected via channel 20 to ports 16 and a reaction chamber comprising sections 22A and 22B. The presence of amplified polynucleotide product in a sample will influence the flow characteristics within the flow channels. The channels 40 in this embodiment are symmetrically disposed and have a progressively narrower diameter towards the center of the pattern. Flow through this channel pattern is sensitive to changes in fluid viscosity caused by the presence of amplified polynucleotide product. Alternatively a more complex channel flow system may be utilized, as illustrated in FIG. 13. FIG. 13 illustrates a pair of flow channel systems 40A and 40B. Channel system 40A is constructed with progressively narrower flow channels towards the center of the pattern, resulting in an enhanced sensitivity to flow restriction.

Flow restriction can be detected, e.g., optically, through a transparent cover over the detection region. Alternatively, one or more pressure sensors may be utilized to detect pressure changes due to changes in fluid properties caused by the accumulation of amplified polynucleotide in or beyond the restricted flow paths. Changes in conductivity upon polynucleotide amplification also may be readily detected through electrical conductivity sensors in contact with the flow region. For example, clogging of the restricted region 40, which blocks flow from inlet port 16A to outlet port 16B, could be detected by a conventional conductivity probe 17 whose output is indicative of the presence or absence of aqueous fluid in the outflow channel. Binding moieties such as labeled antibodies or polynucleotide probes may be included in the restricted flow region, e.g., immobilized, or on a solid phase reactant such as a bead, to bind to the amplified polynucleotide to induce flow reduction restriction in the restricted flow path.

In one embodiment, the mesoscale flow system includes a chamber for lysing cells from a sample in preparation for downstream polynucleotide analysis. The devices also may include a region adapted to separate a particular type of cell in a heterogeneous cell population. The cell separation region includes binding moieties immobilized on structures within the substrate which selectively and reversibly bind a target cell via a characteristic cell surface molecule such as a protein. Other cells in the sample pass downstream and are channelled into a sump or through an exit port. Flow may be continued to wash the cells, e.g., with a flow of buffer. At higher flow rates and pressures, or by changing the solvent composition, the washed cells are released from the structures on which they were immobilized, and thereafter move from the cell separation region downstream to a lysis means, which lyses the cells prior to PCR analysis of intracellular. RNA or DNA.

Figure 9:
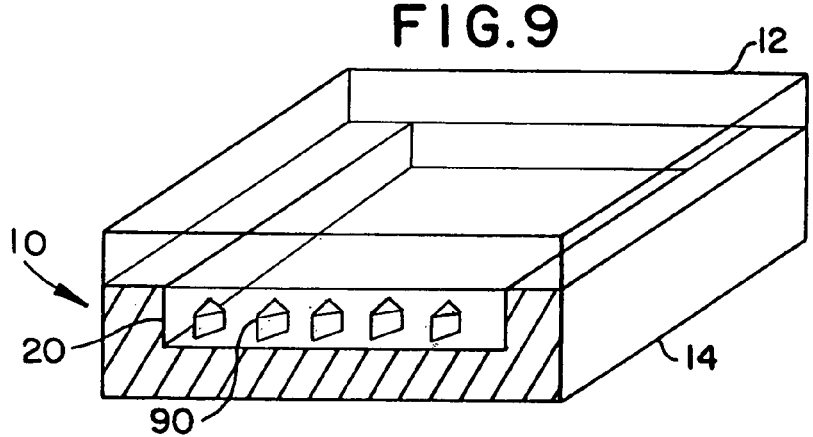
FIG. 9 is a cross sectional perspective view of a flow channel 20 in substrate 14 with cell piercing protrusions 90 extending from a wall of the channel.

The cell lysing means typically is disposed in the flow path between the cell separation region (if any) and the polynucleotide amplification reaction chamber to allow the cells to be lysed prior to analysis for an intracellular polynucleotide. As illustrated in FIG. 9, the cell lysing means may comprise cell membrane piercing protrusions 90 extending from a surface of a flow channel 20. As fluid flow is forced through the piercing protrusion 90, cells are ruptured. In another embodiment, the cell lysis means may simply comprise a region of restricted cross-sectional dimension which implements cell lysis upon application of sufficient flow pressure. The cell lysis means may also comprise sharp edged pieces of silicon trapped within a mesoscale lysis chamber. An appliance which includes means, such as a pump, for forcing the cell containing sample into the cell lysis means, causes cell lysis upon application of sufficient flow pressure, and subsequently delivers the sample through the flow system to the reaction chamber. In another embodiment, the cell lysis means may comprise a cell lysing agent. Cell lysing agents known in the art may be utilized.

Figure 8:
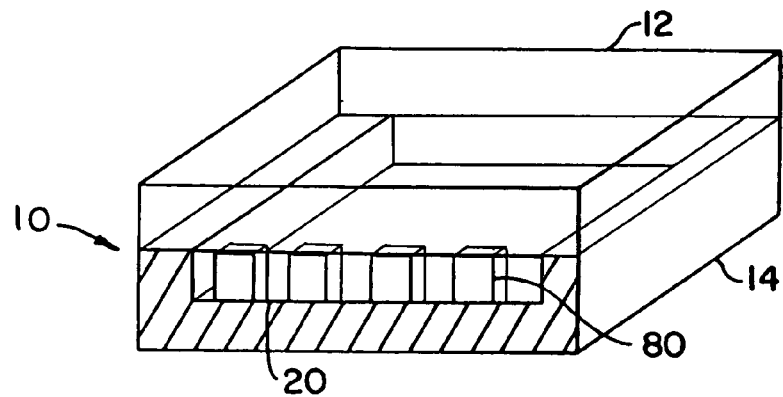
FIG. 8 is a cross sectional perspective view of a flow channel 20 in substrate 14 with cell or debris filtering protrusions 80 extending from a wall of the channel.
Figure 14:
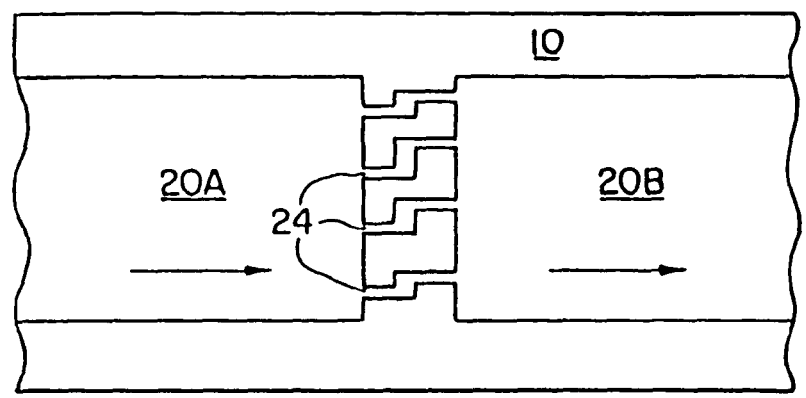
FIGS. 14, 15 and 16 illustrate top plan views of different embodiments of a mesoscale filter 24 microfabricated in flow channel 20 in an analytical device 10.
Figure 15:
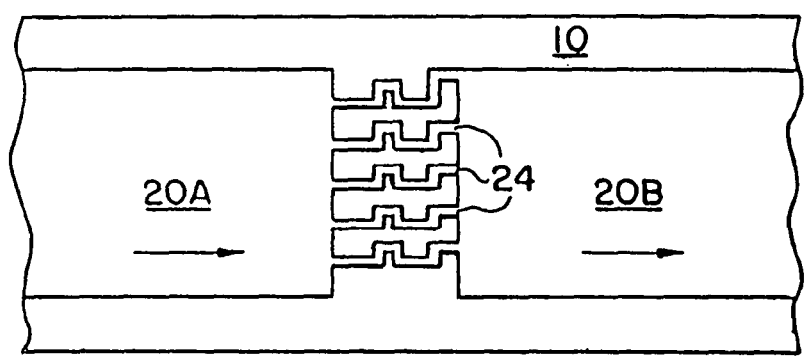
Figure 16:
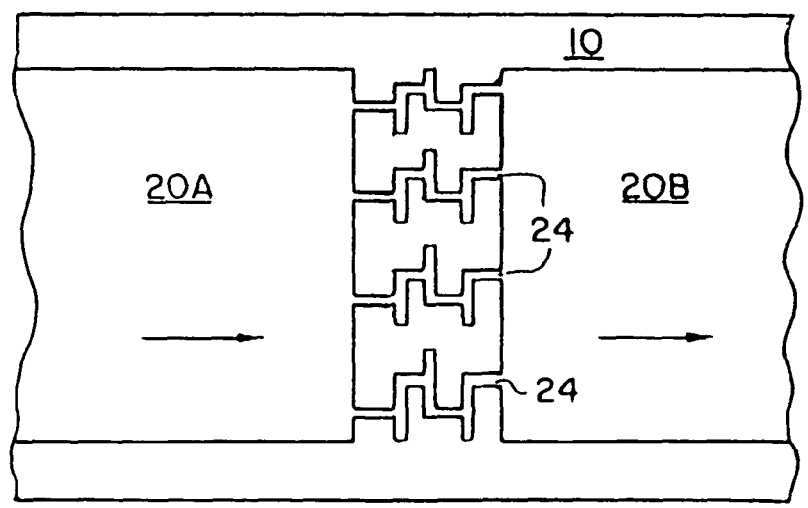

Reagents may be added to the reaction chamber from a separate inlet port in the substrate in fluid communication with the reaction chamber. A filter, microfabricated in the flow channel on the substrate, can be used to filter cell debris prior to polynucleotide analysis. In one embodiment, shown in FIGS. 14, 15 and 16, the filter 24 in device 10 may comprise a mesoscale flow channel of reduced diameter in comparison with channel 20. In operation, sample flows from sample flow channel 20A through filter 24. Sample filtrate then exits filter 24 and flows through channel 20B. The filter 24 is microfabricated with straight or tortuous channels having preferred depths and widths on the order of 0.1 to 50 µm, and span flow channels 20A and 20B, which have maximum depths and widths on the order of approximately 500 µm. As illustrated in FIG. 8, the surface of a flow channel 20 may also include protrusions 80 constituting a cellular sieve for separating cells by size upstream from the PCR analysis chamber. As cell samples are flowed through the flow channel, typically under low pressure, only cells small enough to pass between the protrusions 80 reach downstream functional elements. These cells subsequently can be delivered through a cell lysis region, then to a polynucleotide amplification reaction chamber for analysis.

In another embodiment, paramagnetic or ferromagnetic beads may be provided within the mesoscale flow system, which can be moved along the flow system by an external magnetic field, e.g., in the appliance. The beads may be used to transport reagents between functional elements in the device, or to displace a sample, a reagent or a reaction mixture. In one embodiment, a polynucleotide probe may be immobilized on the magnetic beads enabling the beads to bind to amplified polynucleotide. Magnetic beads comprising a" coating of polynucleotide probe may be transported through the flow system to the reaction chamber at the end of an assay to bind to the amplified polynucleotide product. The bound amplified polynucleotide then may be transported on the magnetic beads to a detection or purification chamber in the flow system, or to a collection port.

G. Exemplary Apparatus

Figure 10A:
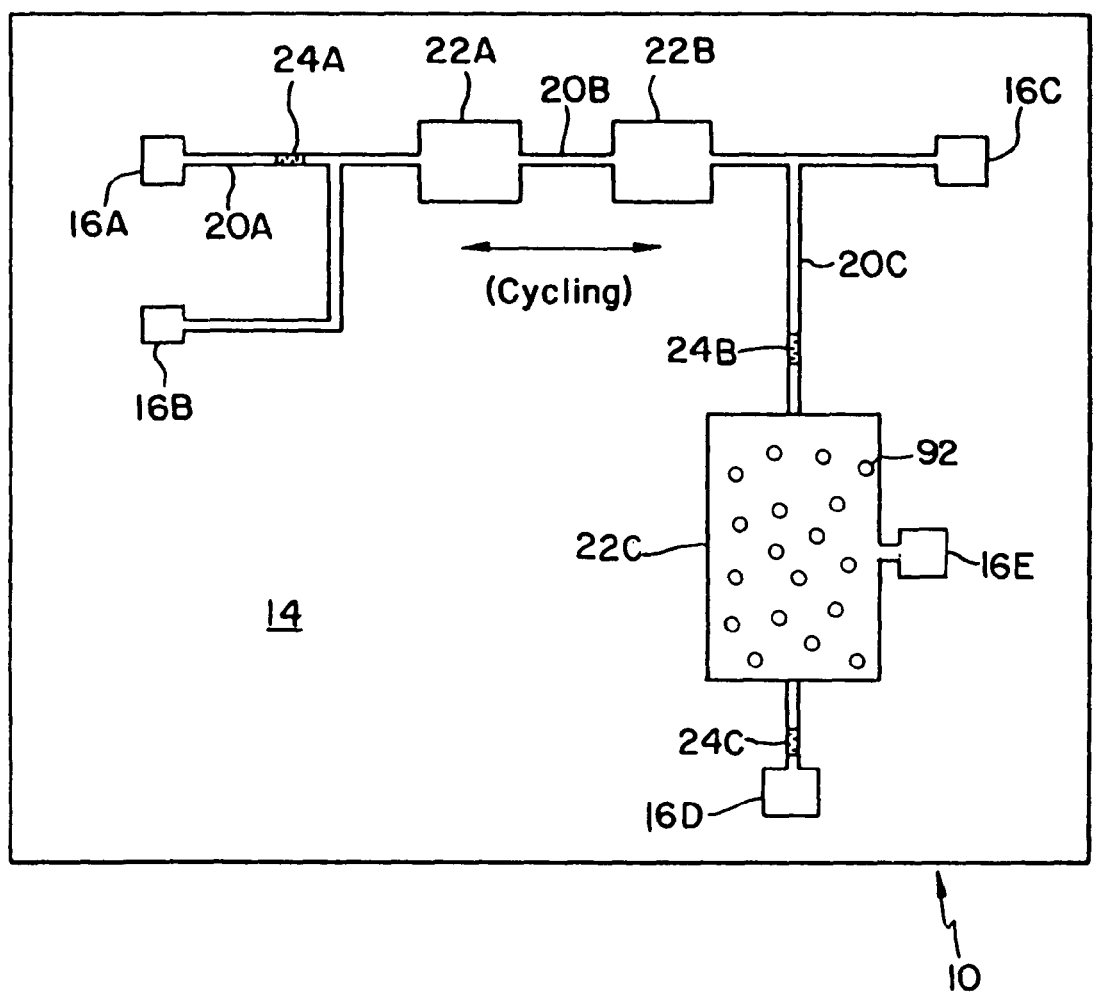
FIG. 10A is a schematic plan view of a mesoscale analytical device including reaction chamber sections 22A and 22B, and detection chamber 22C, microfabricated in the substrate 14.

One embodiment of the invention, illustrated in FIG. 10, is a device 10 comprising a substrate 14 microfabricated with a mesoscale polynucleotide amplification chamber comprising sections 22A and 22B, which are connected by flow path 20B. The device 10 is used in combination with an appliance, such as appliance 50, shown in FIG. 6A, which contains a nesting site for holding the device. The appliance 50 is provided with flow paths 56 mated to ports 16A, 16B, 16C, and 16D in device 10. The appliance also includes valves that allow the ports 16A, 16B, 16C and 16D to be mechanically opened and closed. Port 16E is included for adding reagents to detection chamber 22C. In one embodiment, the flow systems of the devices may be maintained at a hydraulically full volume, and valves in the appliance, or alternatively, in the devices, may be utilized to direct fluid flow. Sections 22A and 22B of the PCR chamber are heated to, e.g., 94° C. and 40-65° C., respectively, to provide a melting temperature and an annealing temperature as required for PCR and other thermally-dependent amplification reactions. As discussed above, reaction chamber sections may be heated by means of an electrical element integrated in the substrate below the sections, which can mate with electrical elements in the appliance. Alternatively, an optical laser may be used to heat the reaction chamber sections through a glass cover disposed over the substrate. A heat sensor may be provided in the substrate, in electrical contact with the appliance. A microprocessor in the appliance can be used to control the temperature of the reaction chamber sections and the flow of fluid in the flow system.

The flow channels of device 10 are fitted with filters 24A, 24B and 24C. Filter 24A is designed to prevent cellular debris and other unwanted particulate matter in the sample from entering the reaction chambers. Filters 24B and 24C are included for the purpose of restraining the complex-forming agent (i.e. beads 92) within detection chamber 22C. Accordingly, filters 24A, 24B and 24C need not be identical.

In operation, for a thermally dependent amplification reaction such as PCR, initially, with the channels and chambers full of buffer, port 16A and 16C are open while 16B and 16D are closed. A pump 52 in the appliance delivers the sample fluid and/or reagents required for amplification, such as Taq polymerase, primers and nucleoside triphosphates, via port 16A, through filter 24A, to reaction chamber section 22A. Port 16A next is closed and 16B is opened, and the pump 52 in the appliance is used to reciprocate fluid flow in cycles through flow channel 20B between section 22A, where polynucleotide dehybridization occurs, and section 22B, where annealing and polymerization occur. Port 16C can be used to vent the system, and also optionally to deliver Taq polymerase, nucleoside triphosphates, primers, and other reagents. When the amplification cycling reaction is terminated, e.g., after 30-35 cycles, port 16C is closed, port 16D is opened, and the pump in the appliance is actuated to deliver the reaction products from reaction chamber sections 22A and 22B to detection chamber 22C, which contains, e.g., a polynucleotide complementary to the amplified sense and/or antisense strand, immobilized on beads 92. Amplification product is detected by observing the agglutination of beads 92, e.g., visually through a" transparent cover disposed over the detection region.

Figure 10B:
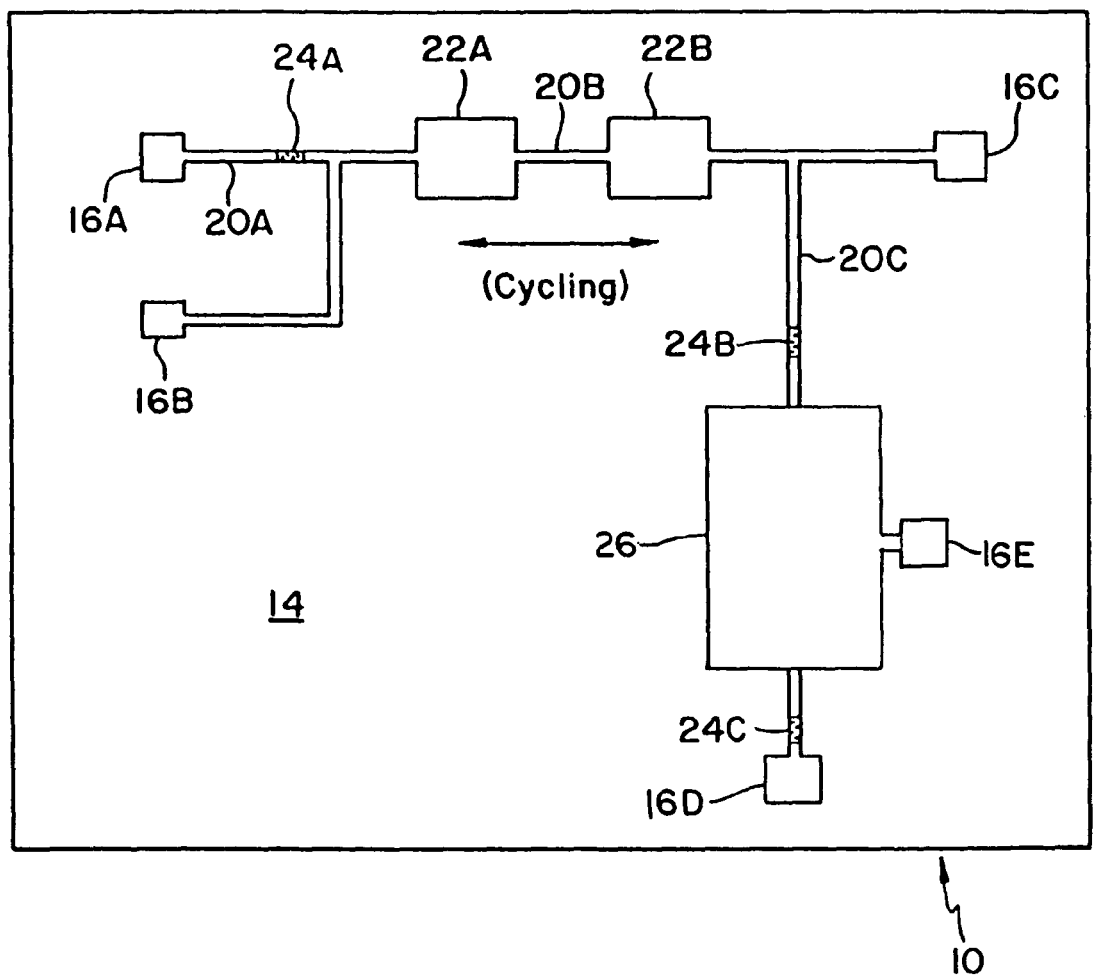
FIG. 10B is a schematic plan view of another mesoscale analytical device including reaction chamber sections 22A and 22B, and detection region 26, microfabricated in the substrate 14.

Another embodiment is illustrated in FIG. 10B. The function, structure and operation of this device is similar to that shown in FIG. 10A, except that it comprises a detection region 26, wherein channels or arrays (not shown) may be fabricated for performing electrophoretic separation of the polynucleotide amplification product. The device includes a port 16E for adding or withdrawing materials from the detection region. The device is used in combination with an appliance similar to appliance 50, shown in FIG. 6A, which further comprises a means for applying an electric field across detection region 26.

Figure 11:
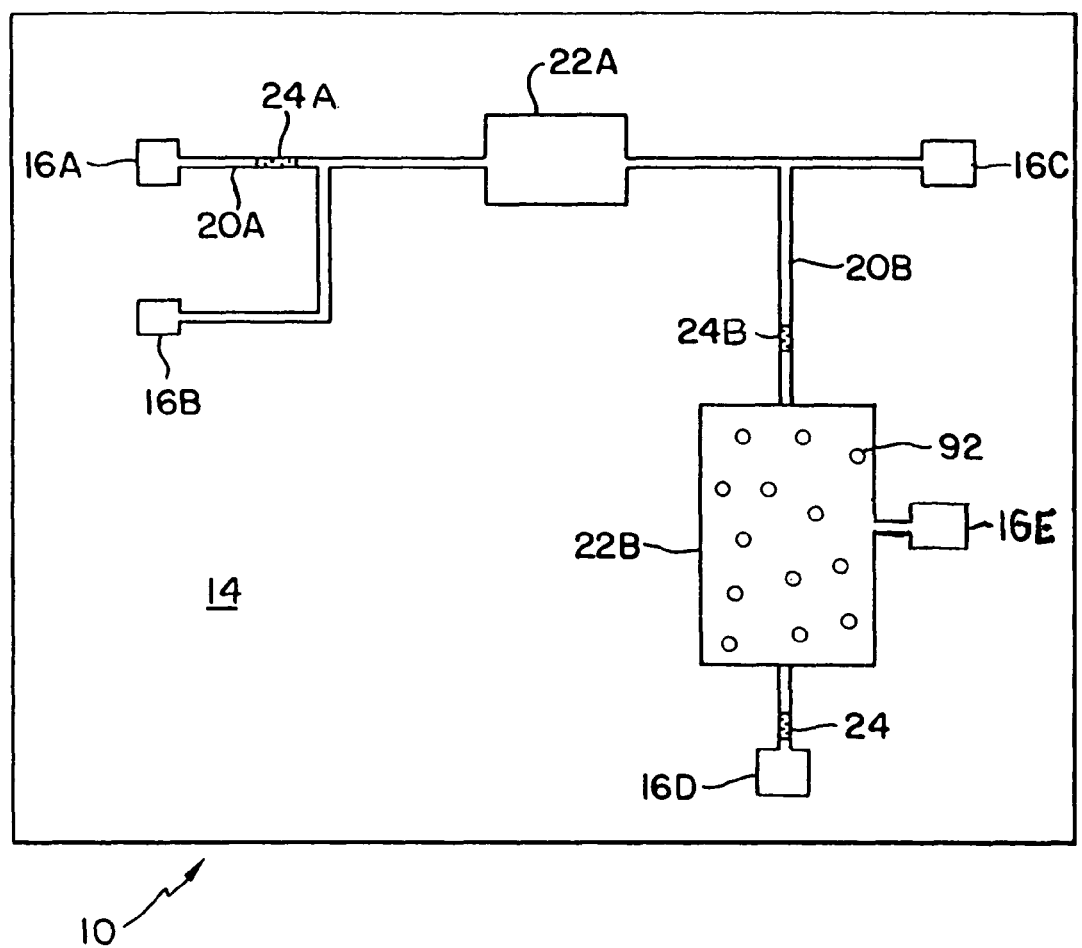
FIG. 11 is a schematic plan view of another mesoscale analytical device including a reaction chamber 22A microfabricated in the substrate 14.

Another embodiment is illustrated in FIG. 11. The function, structure, and operation of this device is identical to that shown in FIG. 10, except that it comprises a single reaction chamber 22A. The device is used in combination with an appliance such as appliance 50 shown in FIG. 3A. The device includes means for heating and cooling reaction chamber 22A alternatively to a temperature required for melting and a temperature required for annealing and polymerization.

In operation, the appliance is used to deliver a sample containing polymerase and other reagents required for reactions such as PCR through inlet port 16A to reaction chamber 22A. Ports 16A and 16D are then closed using a valve connected in the appliance. The heating element in the appliance is then utilized to thermally cycle the reaction chamber between a temperature suitable for dehybridization and temperatures suitable for annealing and polymerization. When the amplification cycles are terminated, ports 16B and 16D are opened and the sample is delivered to detection chamber 22B which contains a polynucleotide probe, e.g., immobilized upon beads 92 or another solid substrate. A positive assay for the polynucleotide is indicated by agglutination of the solid substrate (e.g., beads) in the detection chamber. In the embodiment shown in FIG. 10B, the contents of reaction chamber sections 22A and 22B are delivered to detection region 26, where the polynucleotide product is electrophoretically separated and identified.

The invention will be understood further from the following, nonlimiting examples.

Example 1

A polymerase chain reaction is performed in the device illustrated schematically in FIG. 11, provided with a mesoscale reaction chamber 22A. To perform a PCR analysis to detect a polynucleotide in a cell, a sample cell lysate is added to a buffered solution of Taq polymerase, nucleoside triphosphates, polynucleotide primers and other reagents required for PCR. The cell sample lysate is delivered via the appliance through entry port 16A to PCR reaction chamber 22A. Ports 16A and 16D are closed by means of valves included in the appliance. A microprocessor and temperature control element in the appliance are used to implement a temperature cycle in reaction chamber 22A between 94° C., for polynucleotide dehybridization, 40-60° C. for annealing and 70-75° C. for primer extension.

After the polymerase chain reaction is complete, ports 16B and 16D are opened, and the pump in the appliance connected to port 168 used to deliver the sample from the PCR reaction chamber 22A through flow channel 20B to the detection chamber 22B. Detection chamber 22B contains beads 92 comprising a surface immobilized complementary polynucleotide capable of binding the amplified polynucleotide. The agglutination of the beads caused by hybridization reaction between the amplified polynucleotide and the complementary polynucleotide is observed through a window disposed over the detection region 22B, and provides a test for the presence of amplified polynucleotide product.

Example 2

Figure 12:
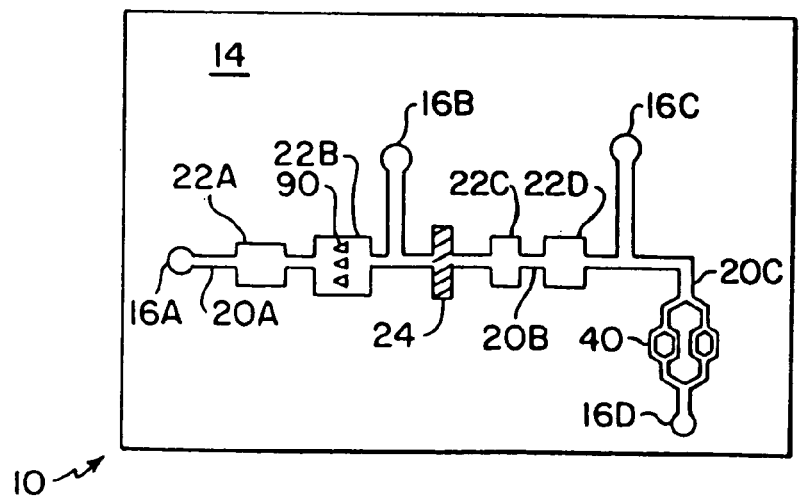
FIG. 12 is a schematic plan view of an analytical device fabricated with a series of mesoscale chambers suitable for implementing a variety of functions including cell sorting, cell lysing and polynucleotide analysis.

FIG. 12 depicts schematically a device 10 including substrate 14 used to separate a nucleic acid from a subpopulation of cells in a mixture in a biological fluid sample, and then to perform an assay for a particular nucleotide sequence. Microfabricated on device 10 is a mesoscale flow path 20 which includes a cell separation chamber 22A, a cell lysis chamber 22B, filter region 24, a PCR reaction chamber comprising sections 22C and 22D, and a restricted flow detection region 40. The mesoscale flow system 20 is also provided with fluid entry/exit ports 16A, 16B, 16C and 16D. The device is used in combination with an appliance, such as appliance 50, shown in FIG. 6A.

Initially, the valves in the appliance are used to close ports 16C and 16D, while ports 16A and 16B are open. A sample containing a mixture of cells is directed to the sample inlet port 16A by the pump 52 in the appliance, and flows through the mesoscale flow path 20 to separation chamber 22A. Chamber 22A contains binding moieties immobilized on the wall of the chamber which selectively bind to a surface molecule on a desired type of cell in the sample. Remaining cellular components exit the substrate via port 16B. After binding of the desired cell population in chamber 22A, flow with buffer is continued, to wash and assure isolation of the cell population. Next part 16B is closed and 16C is opened. Flow is then increased sufficiently to dislodge the immobilized cells. Flow is continued, forcing cells through membrane piercing protrusions 90 in chamber 22B, which tear open the cells releasing intracellular material.

Sample flow continues past filter 24, which filters off large cellular membrane components and other debris, to mesoscale PCR chamber section 22C, which is connected to PCR chamber section 22D by flow channel 20B. Taq polymerase, primers and other reagents required for the PCR assay next are added to section 22D through port 16B from a mated port and flow path in the appliance, permitting mixing of the intracellular soluble components from the separated subpopulation of cells and the PCR reagents. With port 16A closed, a pump in the appliance connected via port 16B is used to cycle the PCR sample and reagents through flow channel 20B between sections 22C and 22D, set at, e.g., 94° C. and 65° C. respectively, to implement plural polynucleotide melting, annealing and polymerization cycles, enabling the amplification of product polynucleotide. Alternatively, all ports may be closed during the amplification reaction and thermal cycling may be performed as described in Example 1 above. The valves in the appliance next are used to open port 16D. The pump in the appliance connected to port 16B is then used to direct the amplified polynucleotide isolated from the cell population to a detection region comprised of a bifurcating series of flow paths 40. Flow restriction in the detection region 40 serves as a positive indicator of the presence of amplified polynucleotide product and is detected optically through a glass cover disposed over the detection region.

Example 3

The amplification of a sample polynucleotide, (bacteriophage lambda DNA) in a mesoscale reaction chamber, having dimensions of 80 μm in depth, 8 mm in width and 14 mm in length, fabricated in a silicon substrate and passivated using different passivation methods was examined.

To conduct the reaction, PCR reagents (e.g., nucleotides, AmpliTaq DNA polymerase, primer and the bacteriophage lambda DNA sample) were mixed in tubes and transferred to the mesoscale reaction chamber in the silicon substrate. The final concentrations of the reactants were: nucleotides, 200 mM each, Taq polymerase, 0.25 U/10 ml; primers, 1.0 mM each; DNA template, 0.1 ng per 10 ml. The thermal cycling (normally 35 cycles) was performed automatically using a computer controlled Peltier heater-cooler.

Figure 23:
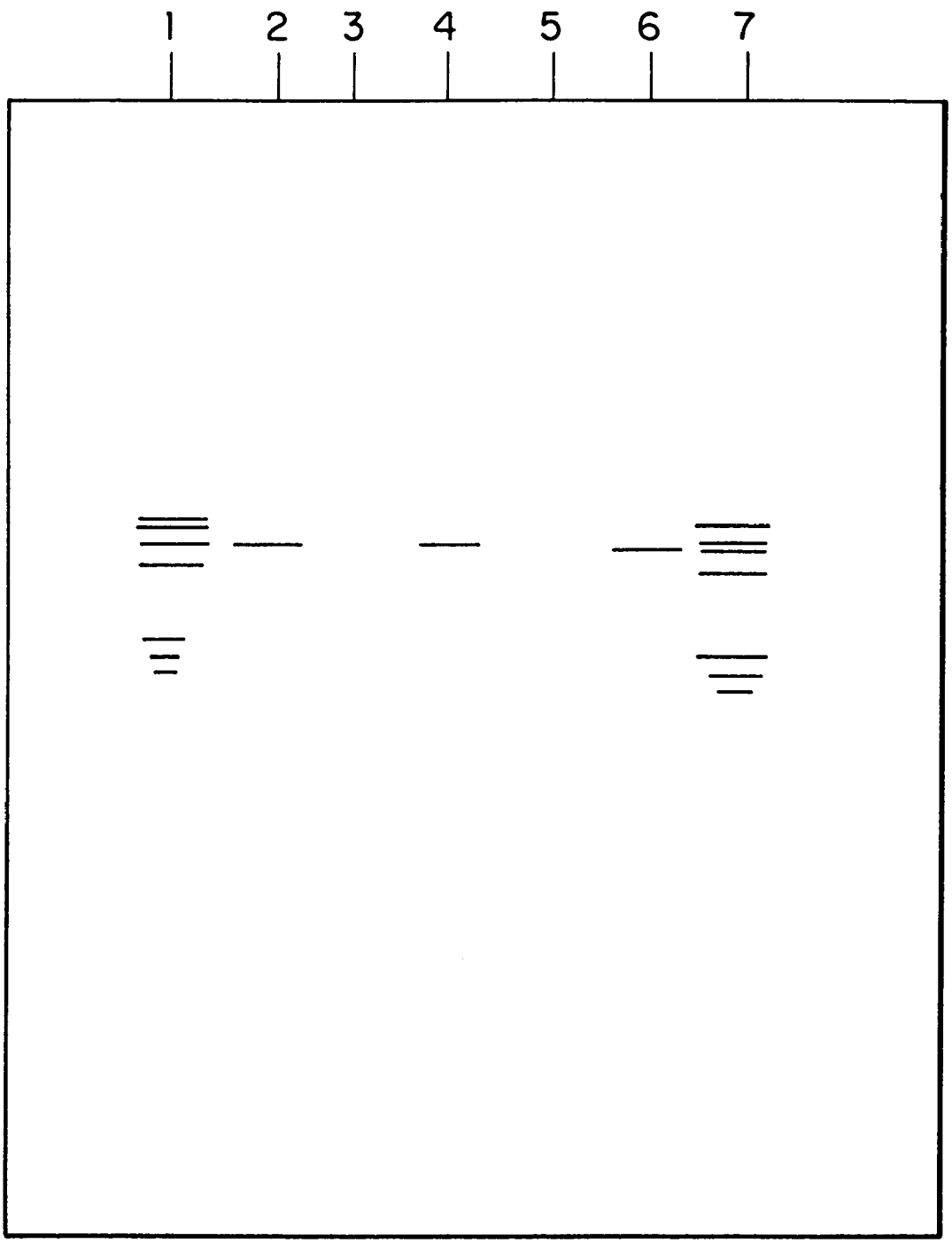
FIG. 23 is a drawing illustrating an agarose gel electrophoresis pattern of polynucleotide samples amplified in a mesoscale amplification chamber.

The results of this PCR reaction using different methods of passivation of the walls of the mesoscale reaction chamber fabricated in the silicon substrate are illustrated in FIG. 23. FIG. 23 is a drawing of an agarose gel containing ethidium bromide, after electrophoresis of the reaction products in the gel. The lanes in the gel correspond as follows: (1 and 7) molecular weight markers (1000, 750, 500, 300, 150 and 50 bp); (2) products of a control amplification reaction conducted in a Perkin-Elmer Model 9600 thermal cycler; (3) products of an amplification reaction in an untreated reaction chamber; (4) products of an amplification reaction in the reaction chamber having a thermal silicon oxide film on the wall surfaces, (5) products of an amplification reaction in the reaction chamber having a silicon nitride coating on the surface formed by a plasma-enhanced chemical vapor deposition (PECVD) process using mixture of silane and ammonia; and (6) products of an amplification reaction in a reaction chamber having a surface coating of a silicon oxide film formed by the PECVD process. Methods for the thermal oxidation of silicon are described, e.g., in Runyan and Bean, "Semiconductor Integrated Circuit Processing Technology," "Addison-Wesley Publishing Co., 1990, Chapter 3. Methods for depositing films on surfaces by a plasma-assisted chemical vapor disposition process are described, e.g., in Sze, "VLSI Technology," McGraw-Hill Book Co., 1983, Chapter 3.

As illustrated in FIG. 23, the reaction product was substantially increased in the silicon reaction chambers provided with a thermal oxide coating (lane 4) or a PECVD oxide coating (lane 6) in comparison to the untreated silicon reaction chamber (lane 3). In contrast, the silicon nitride coating (lane 4) had no positive passivation effect on the amplification reaction.

Example 4

A mesoscale polynucleotide amplification reaction chamber fabricated in a silicon substrate is provided with a coating to passivate the chamber wall surfaces.

A silicon substrate is provided which is fabricated with fluid inlet and outlet ports and a mesoscale flow system including a flow channel, in fluid communication with the ports, and a polynucleotide amplification reaction chamber. The mesoscale amplification reaction chamber, having dimensions of 80 μm in depth, 8 mm in width, and 14 mm in length, is treated with a siliconizing reagent and optionally a macromolecule to form a coating which passivates the silicon surface. The amplification chamber is filled with a siliconizing reagent such as AquaSil™ or Surfasil$^{ml}$ (Pierce, Rockford, Ill. or Sigmacote™ (Sigma Chemical Co., St. Louis, Mo.) using a 100 µl pipette and applying a negative pressure to the exit hole of the chip. The siliconizing reagent is allowed to remain in the chip for at least about 30 min. at room temperature. A constant negative pressure is applied to the exit port to remove the siliconizing reagent, for at least about four hours. About 100 µl of distilled water or 0.1 µl TE buffer is delivered through the flow system via the inlet port to the amplification chamber, using a 100 µl pipette, and a negative pressure is applied to the exit port. The wash is repeated about 6 times. After the last wash, negative pressure is applied to the exit port for about 10 to 15 minutes to drain the channels.

Alternatively, the amplification chamber surface is passivated with a silanization reagent such as dimethyldichlorosilane (DMDCS) or dimethylchlorosilane (DMCS). Methods which can be used for treating surfaces with siliconization or silanization agents are described, e.g., in Pierce, "Instructions: Siliconizing Agents," Rockford, Ill., 1993, the disclosure of which is incorporated herein by reference.

The amplification reaction chamber then optionally is filled with a solution of a blocking agent comprising macromolecule (about 10 mg/ml of macromolecule in 0.1 M Tris buffer, pH 8.6), e.g., an amino acid polymer (see Table 2), via the inlet port using a 100 µl pipette and applying a negative pressure to the exit port. The macromolecule solution is permitted to remain in the amplification chamber for at least'about 1 hr at 4° C. A negative pressure then is applied to the exit port of the device for about 10 to 15 min. This provides a coating of the macromolecule noncovalently associated with the silicone treated surface.

Example 5

The effectiveness of different coatings in diminishing the inhibitory effect of silicon on a polynucleotide amplification reaction was tested.

A sample of silicon powder was coated with Surfasil™ (Pierce, Rockford, Ill.) or Sigmacote™ (Sigma Chemical Co., St. Louis, Mo.) and allowed to dry. The silicon particles then were coated with a variety of different macromolecules (obtained from Sigma Chemical Co., St. Louis, Mo.) listed in Table 2, as described in Example 4. About 4 mg of each coated silicon preparation was then placed into separate reaction tubes containing 45 µl of a PCR reaction mixture (see Example 3) and run in a Perkin Elmer Model 9600 thermal cycler.

Additionally, a mesoscale reaction chamber having dimensions of 80 µm in depth, 8 mm in width, and 14 mm in length, was provided with a coating of a silanization reagent or siliconization reagent associated with different macromolecules (Table 2), according to the procedure described in Example 4. A PCR reaction was conducted in the coated reaction chambers using the reagents as described in Example 3. The results using different coatings are shown in Table 2, using a rating scale of 0 to 4, where the positive control (run in the GeneAmp 9600) has a rating of 3. As illustrated in Table 2, the most effective coating was Surfasil™ (Pierce, Rockford, Ill.) in combination with polyvinylpyrrolidone or polyadenylic acid.

TABLE 2

| No. | Silicone Agent/Macromolecule | Rating of Effectiveness on Silicon Powder | Rating of Effectiveness on PCR Chip |
|---|---|---|---|
| 1. | Sigmacote ™/Poly-L-alanine | 2 | - |
| 2. | Sigmacote ™/Poly-L-aspartic acid | 0 | - |
| 3. | Sigmacote ™/Polyglycine | 3 | >1 |
| 4. | Sigmacote ™/Poly-L-leucine | 3 | 0 |
| 5. | Sigmacote ™/Poly-L-phenylalanine | 2 | - |
| 6. | Sigmacote ™/Poly-L-tryptophan | 2 | - |
| 7. | Sigmacote ™/Poly-L-lysine | 0 | - |
| 8. | Sigmacote ™/Polyvinylpyrrolidone | >1 | - |
| 9. | Sigmacote ™/Polyadenylic acid | 4 | 0 |
| 10. | Siginacote ™/Polymaleimide | 0 | - |
| 11. | Sigmacote ™/Maleimide | 1 | - |
| 12. | Surfasil ™/Poly-a-alanine | 3 | 2 |
| 13. | Surfasil ™/Poly-L-aspartic acid | 0 | - |
| 14. | Surfasil ™/Polyglycine | 1 | - |
| 15. | Surfasil ™/Poly-L-leucine | 2 | - |
| 16. | Surfasil ™/Poly-L-phenylalanine | 2 | - |
| 17. | Surfasil ™/Poly-L-tryptophan | 1 | - |
| 18. | Surfasil ™/Poly-L-lysine | 0 | - |
| 19. | Surfasil ™/Polyvinylpyrrolidone | 4 | 2 to 3 |
| 20. | Surfasil ™/Polyadenylic acid | 4 | 3 to 4 |
| 21. | Surfasil ™/Polymaleimide | 0 | - |
| 22. | Surfasil ™/Maleirnide | 1 | - |
| 23. | Uncoated Silicon | 0 | 0 to 2 |
| 24. | Surfasil ™ | 3 | 0 to 1 |
| 25. | Sigmacote ™ | 2 | - |
| 26. | DMDCS | - | 0 |
| 27. | DMDCS/polyadenylic acid | - | 1 |
| 28. | AquaSil ™ in H$_2$O 1:99 | - | 1 |

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. A device for amplifying a polynucleotide in a sample by conducting a polynucleotide amplification reaction, the device comprising a solid substrate microfabricated to define:
    a sample inlet port;
    a mesoscale flow system comprising;
    a sample flow channel extending from said inlet port; and
    a polynucleotide amplification region of the device, in fluid communication with said flow channel, said region having at least one cross-sectional dimension of width or depth of about 0.1 to 1000 microns, at least said polynucleotide amplification region being permanently sealed with a cover; and
an appliance for use in combination with said substrate, said appliance including a nesting site for receiving said substrate and a conduit in fluid communication with the inlet port of said substrate.

2. The device of claim 1 wherein the polynucleotide amplification region comprises a reaction chamber which has at least one dissimilar cross-sectional dimension from a cross-sectional dimension of the sample flow channel.

3. The device of claim 1 wherein said polynucleotide amplification region is configured to contain at least one reagent for conducting a polymerase chain reaction.

4. The device of claim 1 wherein said polynucleotide amplification region is configured to contain at least one reagent for conducting a ligase chain reaction.

5. The device of claim 1 wherein said polynucleotide amplification region is configured to contain at least one reagent for conducting an isothermal DNA amplification reaction.

6. The device of claim 1 wherein said polynucleotide amplification region of the device has at least one cross-sectional dimension of width or depth of about 0.1 to about 500 microns.

7. The device of claim 1 wherein said polynucleotide amplification region of the device has at least one cross-sectional dimension of width or depth of about 0.1 to about 100 microns.

8. The device of claim 1 wherein said polynucleotide amplification region of the device has at least one cross-sectional dimension of width or depth of about 2 to about 50 microns.

9. The device of claim 1 further including means for thermally cycling the contents of said amplification region whereby in each cycle the temperature is controlled to dehybridize double stranded polynucleotide and to permit the in vitro amplification of the sample polynucleotide.

10. The device of claim 9, wherein said means for thermally cycling comprises an electromagnetic energy source, said electromagnetic energy source being provided in said appliance.

11. The device of claim 1, further comprising a pump actuable to cause fluid flow through the flow system of said substrate.

12. A device of claim 1, wherein said pump is disposed in said appliance and connected to said conduit.

13. A method for amplifying a polynucleotide in a sample by conducting a polynucleotide amplification reaction, the method comprising:

(i) providing a device comprising
    a solid substrate microfabricated to define:
    a sample inlet port;
    a mesoscale flow system comprising:
    a sample flow channel extending from said inlet port; and
    a polynucleotide amplification region, in fluid communication with said flow channel, said region having at least one cross sectional dimension of width or depth of about 0.1 to 1000 microns, at least said polynucleotide amplification region being permanently sealed with a cover; and
an appliance for use in combination with said substrate, said appliance including a nesting site for receiving said substrate and a conduit in fluid communication with the inlet port of said substrate;

(ii) delivering through said conduit, said inlet port and said sample flow channel to said polynucleotide amplification region, said sample polynucleotide and at least one reagent required for the polynucleotide amplification reaction; and (iii) thermally controlling the contents of the amplification region to amplify said polynucleotide.

14. The method of claim 13 wherein said delivering comprises delivering at least one reagent for conducting a polymerase chain reaction.

15. The method of claim 13 wherein said delivering comprises delivering at least one reagent for conducting a ligase chain reaction.

16. The method of claim 13 wherein said delivering comprises delivering at least one reagent for conducting an isothermal DNA amplification reaction.

* * * * *